United States Patent [19]

Murray

[11] Patent Number: 4,689,437

[45] Date of Patent: Aug. 25, 1987

[54] OLIGOMERIZATION TO ALPHA-OLEFINS

[75] Inventor: Rex E. Murray, Charleston, W. Va.

[73] Assignee: Union Carbide Corporation, Danbury, Conn.

[21] Appl. No.: 887,183

[22] Filed: Jul. 21, 1986

[51] Int. Cl.$^4$ ............................ C07C 2/02; C07C 2/36
[52] U.S. Cl. .................................... 585/526; 585/514; 585/515; 585/527; 502/155; 502/162; 502/165; 502/167; 502/117
[58] Field of Search ............... 502/155, 117, 162, 165, 502/167; 585/514, 515, 526, 527

[56] References Cited

U.S. PATENT DOCUMENTS

| | | | |
|---|---|---|---|
| 3,676,523 | 7/1972 | Mason | 260/683.15 D |
| 3,737,475 | 6/1973 | Mason | 160/683.15 D |
| 4,293,727 | 10/1981 | Beach et al. | 585/515 |
| 4,310,716 | 1/1982 | Beach et al. | 585/515 |
| 4,382,153 | 5/1983 | Beach et al. | 585/515 |
| 4,487,847 | 12/1984 | Knudsen | 502/155 |

FOREIGN PATENT DOCUMENTS

| | | | |
|---|---|---|---|
| 9379497 | 7/1955 | Fed. Rep. of Germany | |
| 1538950 | 9/1968 | France | 585/527 |
| 4151948 | 5/1978 | Japan | 502/117 |

Primary Examiner—Asok Pal
Attorney, Agent, or Firm—Saul R. Bresch

[57] ABSTRACT

An olefin oligomerization/cooligomerization process with a catalyst comprising the reaction product of (1) a transition metal compound selected from the metals Ni, Co, Cr, Fe, Cu, (2) a catalyst activator capable of donating a hydride, alkyl, alkenyl or aryl group when the transition metal has the oxidation state of O or the transition metal compound does not have a hydride, alkyl, alkenyl or aryl group, and (3a) an organophosphorus sulfonate ligand containing one benzene ring with trivalent phosphorus P(III) group and SO$_3$M group at ortho-positions, or one benzene ring with CH$_2$—P(III) and CH$_2$—SO$_3$M groups at ortho-positions, or a bridging or fused aromatic ring system with P(III) or CH$_2$—P(III) group and SO$_3$M or CH$_2$—SO$_3$M group at adjacent positions on different rings, or any aromatic ring having the P(III) and SO$_3$M groups at adjacent positions, where M is H, Group IA or Group IIA metals, quarternary ammonium or phosphonium (NR$_4$, PR$_4$) radical, or (3b) a P(III) component connected through $$-(A)_x-(CR^2R^3)_y-$$

group to an SO$_3$M group, where A=0, NH, NR, and R$^2$ and R$^3$ are H or a substituted or unsubstituted hydrocarbyl radical, x=1, 2 and y=1,2,3.

15 Claims, No Drawings

OLIGOMERIZATION TO ALPHA-OLEFINS

TECHNICAL FIELD

This invention relates to an oligomerization process for the production of alpha-olefins and a catalyst therefor.

BACKGROUND ART

Linear alpha-olefins having 4 to 20 carbon atoms are key feedstocks in the production of surfactants, plasticizers, synthetic lubricants, and polyolefins. High purity alpha-olefins are particularly valuable in the production of low density polyethylene and in the oxo process.

The most successful processes for the production of alpha-olefins to date are those catalyzed by nickel complexes of phosphine-carboxylate ligands and sulfonated ylide/nickel type compounds. While these catalysts are quite active and have good selectivity insofar as the production of alpha-olefins is concerned, the art is continuously searching for ethylene oligomerization catalysts, which display higher activity and greater alpha-olefin selectivity and allow for a more economical process.

For example, insofar as economy is concerned, the process utilizing the nickel complexes of phosphine-carboxylate ligands requires three reaction steps; ethylene oligomerization, isomerization of $C_{20+}$ product, and disproportionation of $C_{20+}$ internal olefins to $C_{11}$ to $C_{14}$ internal olefins. The latter two steps are necessary because $C_{20+}$ olefins have little commercial value. The high level of internal olefin production also raises a problem of purity important, as noted, in the production of low density polyethylene and the oxo process. Other disadvantages of these catalysts follow: the ligands are expensive to prepare; polyethylene formation must be guarded against; the catalysts are relatively unstable; solvent is degraded; and ethylene pressure requirements are high. The sulfonated ylide/nickel type catalysts suffer from similar deficiencies.

DISCLOSURE OF INVENTION

An object of this invention, therefore, is to provide a process for oligomerization to alpha-olefins, which (i) utilizes a catalyst having a higher activity than, and an improved selectivity over, its predecessor catalysts and (ii) is more economical than comparable prior art processes.

Other objects and advantages will become apparent hereinafter.

According to the present invention an economic process for the oligomerization of ethylene, or cooligomerization of ethylene and propylene, to alpha-olefins utilizing a catalyst having a substantially higher activity and greater selectivity than catalysts heretofore used for similar purposes has been discovered. The process comprises passing ethylene or a mixture of ethylene and propylene in contact with a catalyst, in the liquid phase, said catalyst comprising the reaction product of (i) a transition metal compound wherein the transition metal is selected from the group consisting of nickel, chromium, cobalt, iron, and copper, and mixtures thereof; (ii) in the event that (a) the transition metal is not in the oxidation state of zero or (b) the transition metal compound does not have a hydride or an alkyl, alkenyl, alkynyl, or aryl group bonded to the transition metal, a catalyst activator consisting of a compound or compounds capable of transferring a hydride or an alkyl, alkenyl, alkynyl, or aryl group from itself to the transition metal/ligand (hereinafter defined) complex formed by the reaction of the transition metal compound with the ligand and bonding the group to the transition metal, said activator being present in a sufficient amount to activate the catalyst; and (iii) at least one organophosphorus sulfonate ligand containing (a) at least one benzene ring having a trivalent phosphorus atom located at one position on the benzene ring and an $SO_3M$ group located at a position on the benzene ring ortho thereto, or at least one benzene ring having a trivalent phosphorus atom connected through a methylene group to a first position on the benzene ring and an $SO_3M$ group connected through a methylene group to a second position on the benzene ring othro to the first position, or at least one bridging or fused aromatic ring system having a trivalent phosphorus atom and an $SO_3M$ group, each located on a different aromatic ring in the system at substituent positions adjacent to one another, or at least one aromatic ring, other than a benzene ring, or heteroaromatic ring, each ring having a trivalent phosphorus atom and an $SO_3M$ group located at substituent positions adjacent to one another, wherein M is selected from the group consisting of hydrogen, alkali metals, alkaline earth metals, and $NR_4$ and $PR_4$ wherein R is a hydrogen atom or a substituted or unsubstituted hydrocarbyl radical having 1 to 15 carbon atoms and each R can be alike or different, or (b) a trivalent phosphorus atom connected through a group having the formula

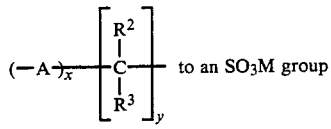

wherein A is an oxygen atom, an NH radical, or an NR radical; $R^2$ and $R^3$ are hydrogen atoms or a substituted or unsubstituted hydrocarbyl radical having 1 to 6 carbon atoms and can be alike or different; x is an integer 0 or 1; y is an integer from 1 to 3; and R and M are as defined above.

DETAILED DESCRIPTION

The products of subject process are chiefly alpha-olefins of even carbon numbers. The molecular weight distribution of oligomers depends upon several reaction variables; however, the structure of the particular ligand used in the catalyst has a strong influence on the result. One catalyst, for example, produces mainly $C_4$ to $C_{12}$ alpha-olefins plus lesser and ever diminishing amounts of higher alpha-olefins resulting in a high overall selectivity to the $C_4$ to $C_{20}$ range. Other catalysts yield higher or lower molecular weight distributions depending mainly on the size of their ligand cone angles. The cone angle is determined as described by C. A. Tolman in the Journal of the American Chemical Society, volume 92, 1970, page 2956 and in Chemical Reviews, volume 77, 1977, page 313. Cone angles are also discussed in U.S. Pat. Nos. 4,169,861 and 4,201,728. The aforementioned publications are incorporated by reference herein. With regard to the ortho-sulfonate aspect of this invention, if one assumes that the ortho-sulfonate group exhibits about the same cone angle effect as an ortho-methyl group, then the calculated cone angles can have an average value in the range of about 120 degrees to about 200 degrees and a preferred average value in the range of about 150 degrees to about 180 degrees. Larger ligand cone angles usually give higher molecular weight distributions when the catalysts are compared under matched reaction conditions. With large cone angle ligands, oligomer distribution usually goes beyond $C_{20}$ in significant proportions. Reactivity increases with increasing cone angle up to 180° and then falls off. Other reaction parameters such as temperature, ethylene pressure, and solvent also influence oligomer distribution. Alpha content is increased by lowering reaction temperature, lowering catalyst concentration, and/or increasing ethylene pressure.

As previously noted, alpha-olefins produced by ethylene oligomerization have even carbon numbers. Subject catalysts are practically inert to propylene; however, when a mixture of ethylene and propylene is present, both even and odd numbered olefins have been observed.

The catalyst is the reaction product of three components, i.e., (i) a transition metal compound (ii) a catalyst activator, and (iii) an organophosphorus sulfonate ligand.

The transition metal compound can be an organometallic compound, an organic salt, or an inorganic salt wherein the transition metal is selected from the group consisting of nickel, chromium, cobalt, iron, copper, and mixtures thereof. The transition metals are preferably in the following oxidation states: nickel—0 or 2, chromium, cobalt, and iron—0, 1, 2, or 3; and copper—0, 1, or 2. Where the compound is a salt, the hydrated form is preferred. Metal salts are preferred, paticularly the halides, sulfonates, benzenesulfonates, and tetrafluoroborates. Useful metal compounds are the chlorides, bromides, iodides, fluorides, hydroxides, carbonates, chlorates, ferrocyanides, sulfates, hexafluorosilicates, trifluoromethanesulfonates, nitrates, sulfides, selenides, silicides, cyanides, chromates, phenoxides, dimethyldithiocarbamates, hexafluoroacetonates, molybdates, phosphates, oxides, stannates, sulfamates, thiocyanates, cyanates, titanates, tungstates, cyclopentadienides, formates, acetates, hydroxyacetates, propionates, hexanoates, oxalates, benzoates, cyclohexanebutyrates, naphthenates, citrates, dimethylglyoximes, acetylacetimides, phthalocyanines, and bis-cyclooctadienes. The nickel salts, particularly those of sulfonate, tetrafluoroborate, and chloride hexahydrate, are preferred. Nickel typically gives the most active catalysts followed by chromium, copper, cobalt, and iron, in that order. Some nickel catalysts are about 50 times more reactive than chromium catalysts. On the other hand, some chromium catalysts have shown very high alpha-olefin selectivities. Mixtures of the various transition metal compounds can be used.

Specific examples of useful transition metal compounds are $NiCl_2$(anhydrous), nickel bis-cyclooctadiene, $NiCl_2.6H_2O$, $Ni(BF_4)_2.6H_2O$ $NiSO_4.6H_2O$, $NiBr_2.xH_2O$, Ni(II)acetylacetonate, $NiCl_2$.dimethoxyethane, $Ni(OH)_2$, hexamminenickel(II) chloride, nickel benzoate, nickel fluoride.$4H_2O$, nickel tosylate.$6H_2O$, nickel acetate.$4H_2O$, chromium(III) chloride.$6H_2O$, chromium(II) chloride, cupric chloride.$2H_2O$, $FeCl_2.4H_2O$, and cobalt(II) acetate.$4H_2O$.

The catalyst activator can be any reagent capable of activating the catalyst under oligomerization conditions. They can be selected from among the cocatalysts well known in the art of ethylene or propylene polymerization or oligomerization. Preferred catalyst acitivators are reagents considered to be capable of transferring a hydride or an alkyl, alkenyl, alkynyl, or aryl group from itself to the metal/ligand complex formed by the reaction of the metal salt with the ligand and bonding the group to the transition metal, said activator being present in a sufficient amount to activate the catalyst. Where the transition metal compound already has a hydride or an alkyl, alkenyl, alkynyl, or aryl group bonded to the transition metal and the metal is in the zero oxidation state, the catalyst activator is not required. Useful activators are borohydrides, aryl boranes, borane ($BH_3$), mono-, di-, and trialkyl boranes, aryl borates, tri and tetra coordinate organoaluminum compounds, aluminum hydrides, tri and tetra alkyl boron compounds, organozinc compounds, and mixtures thereof. The borohydrides can be alkali metal borohydrides, quaternary ammonium borohydrides wherein the ammonium cation is $R_4N^+$, each R being alike or different and selected from the group consisting of hydrogen and alkyl radicals having 1 to 10 carbon atoms; and alkali metal alkoxyborohydrides, phenoxyborohydrides, or amidoborohydrides wherein there are 1 to 3 alkoxy, phenoxy, or amido groups and each group has 1 to 10 carbon atoms. The aryl borane compounds can have 1 to 3 aromatic rings and the aryl borates can have 1 to 4 aromatic rings. All of the various aryl, alkyl, or alkoxy groups can be substituted or unsubstituted. Mixtures of the various boron compounds can be used. Examples are sodium borohydride, potassium borohydride, lithium borohydride, sodium trimethylborohydride, potassium tripropoxy-borohydride, tetramethylammoniumborohydride, triphenylborane, sodium tetraphenylborate, lithium tetraphenylborate, sodium hydrido tris(1-pyrazolyl)borate, potassium dihydro bis(1-pyrazolyl)borate, lithium triethylborohydride, lithium tri-sec-butylborohydride, potassium tri-sec-butylborohydride, sodium cyanoborohydride, zinc borohydride, bis(triphenylphosphine)copper (I) borohydride, potassium tetraphenylborate, lithium phenyltriethylborate, lithium phenyltrimethoxyborate, sodium methoxytriphenylborate, sodium diethylaminotriphenylborate, and sodium hydroxytriphenylborate. In general, boranes derived from olefin hydroboration are suitable. These boranes can be $BH_3$, triethylborane, dicyclohexylborane, t-hexylborane, diethylborane, ethylborane, 9-borabicyclononane [3,3,1]nonane, tricyclohexylborane, and catecholborane. Sodium tetraphenylborate gives a more active catalyst than sodium borohydride, the difference in activity often being twofold. A mixture of triphenyl borane and sodium borohydride gives activities similar to sodium tetraphenylborate. Even though sodium tetraphenylborate gives a more active catalyst than sodium borohydride, sodium borohydride may be economically favored in some circumstances. Certain organophosphorus sulfonates do not appear to be very stable to treatment with borohydrides. Phosphonito sulfonates and phosphito sulfonates are examples. In this case, the use of tetraphenylborate or other organo borates or organo boranes are preferred. Examples of tri and tetra coordinate organoaluminum compounds are triethylaluminum, diisobutylaluminum hydride, diisobutylaluminum chloride, diethylaluminum cyanide, lithium tetrabutylaluminate, sodium tetraphenylaluminate, triphenylaluminum, trimethylaluminum, trisobutylaluminum, tri-n-propylaluminum, diethylaluminum chloride, ethylaluminum dichloride, ethylaluminum sesquichloride, and methylaluminum sesquichloride. Examples of aluminum hydrides are lithium aluminum hydride, diisobutylaluminum hydride, sodium dihydrobis(2-methoxyethoxy)aluminate, lithium diisobutylmethylaluminum hydride, sodium triethylaluminum hydride, lithium trimethoxyaluminum hydride, and potassium tri-t-butoxyaluminum hydride.

The organophosphorus sulfonate ligand contains (a) at least one benzene ring having a trivalent phosphorus atom located at one position on the benzene ring and an SO₃M group located at a position on the benzene ring ortho thereto, or at least one benzene ring having a trivalent phosphorus atom connected through a methylene group to a first position on the benzene ring and an SO₃M group connected through a methylene group to a second position on the benzene ring ortho to the first position, or at least one bridging or fused aromatic ring system having a trivalent phosphorus atom and an SO₃M group, each located on a different aromatic ring in the system at substituent positions adjacent to one another, or at least one aromatic ring, other than a benzene ring, or heteroaromatic ring, each ring having a trivalent phosphorus atom and an SO₃M group located at substituent positions adjacent to one another, wherein M is selected from the group consisting of hydrogen, alkali metals, alkaline earth metals, and NR₄ and PR₄ wherein R is a hydrogen atom or a substituted or unsubstituted hydrocarbyl radical having 1 to 15 carbon atoms and each R can be alike or different, or (b) a trivalent phosphorus atom connected through a group having the formula

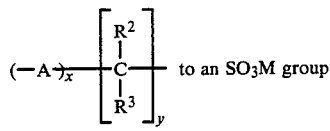
to an SO₃M group wherein A is an oxygen atom, an NH radical, or an NR radical; R² and R³ are hydrogen atoms or a substituted or unsubstituted hydrocarbyl radical having 1 to 6 carbon atoms and can be alike or different; x is an integer 0 or 1; y is an integer from 1 to 3; and R and M are as defined above.

The phosphorus portion of the ligand can be a primary, secondary, or tertiary phosphino, phosphinito, phosphonito, phosphito, or aminophosphino group. The ligands are believed to be chelating or potentially chelating.

The organophosphorus-sulfonate is usually in the alkali metal salt form, e.g., lithium, sodium, or potassium.

Bridging ring systems are exemplified by diphenyl, the adjacent substituent positions being the ortho positions on each ring which are opposite to one another. Fused ring systems are exemplified by napthalene, the adjacent substituent positions being 1 and 8 and 4 and 5. Two aromatic rings that share a pair of carbon atoms are said to be fused.

Additional examples of bridging and fused ring systems are anthracene, phenanthrene, tetralin, 1-phenylnapthalene, chrysene, quinoline, isoquinoline, 1,10-phenanthroline, indole, benzothiophene, acenaphthene, diphenylene, and pyrene.

Typical ortho-phosphinosulfonates can be represented by the following structural formula:

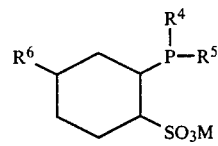

wherein R⁴, R⁵, and R⁶ are hydrogen atoms or substituted or unsubstituted hydrocarbyl radicals having 1 to 20 carbon atoms, preferably 2 to 10 carbon atoms and can be alike or different; R⁴ and R⁵ can be connected to form a heterocyclic radical; and M is as set forth above.

As long as the conditions of being in ortho positions or in adjacent positions are met, the other positions on the aromatic rings can have various substituents, e.g., additional trivalent phosphorus atoms and SO₃M groups and/or substituted or unsubstituted hydrocarbyl radicals having 1 to 20 carbon atoms, preferably 2 to 10 carbon atoms, and the substituents can be alike or different. Thus, the phosphorus to sulfonate ratio does not have to be one to one, but can be, for example, 2 to 1, 1 to 2, and 2 to 4. Illustrative hydrocarbyl radicals are alkyl, aryl, alkoxy, or aroxy. Other substituents can be, e.g., amino or amido groups. Examples of substituents on the rings of the aryl and aroxy radicals are mentioned below. Sulfonated aromatics, which can be converted to the organophosphorous sulfonates useful in subject invention, may be found in the Aldrich Catalog Handbook of Fine Chemicals, 1986-1987, published by Aldrich Chemical Company, Inc., Milwaukee, Wis., on pages 25, 28, 82, 107, 115, 131, 132, 154, 289, 350, 593, 652, 685, 771, 969, 970, 982, 988, 1146, 1147, 1150, 1159, 1199, 1210, 1211, 1266, 1268, and 1278 designated as 21,042-0; 21,043-9; 21,044-7; 20,183-9; 85,740-8; 21,456-6; 21,033-1; 21,057-9; 20,196-0; 20,200-2; 20,193-6; 30,198-7; 21,036-6; 20,194-4; 21,037-4; 14,644-7; A8,680-5; 10,798-0; A9,277-5; B315-9; 25,980-2; 10,814-6; 13,507-0; 19,982-6; 13,369-8; 22,845-1; 22,847-8; 28,995-7; E4,526-0; 18,381-4; H5,875-7; 27,537-5; 25,089-9; N60-5; 18,634-1; 24,954-8; 18,722-4; 27,490-9; 22,519-3; P6,480-4; 27,198-5; 85,616-9; Q150-6; 24,307-8; 24,253-5; 11,273-9; 16,720-7; 26,146-7; 18,495-0; 25,533-5; 10,456-6; T3,592-0; and 16,199-3, all incorporated by reference herein. It should be noted that among the aromatics which underlie the aromatic sulfonates can be aromatics having the basic structural formula of pyridine, quinoline, and thiophene.

Typical alkylene-phosphorus sulfonates can be represented by the following structural formula:

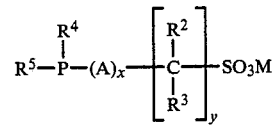

wherein R², R³, R⁴, and R⁵ are set forth above and can be alike or different, and A, M, x, and y are also as set forth above.

R, R², R³, R⁴, R⁵, and R⁶ can, as noted above, be hydrogen atoms, substituted or unsubstituted hydrocarbyl radicals, and alike or different. They can be alkyl, aryl, alkoxy, aroxy, amino, or amido radicals, or mixtures of these radicals. The radicals can be separate from one another or cojoined.

Examples of substituents, which can be present on the rings of the aryl and aroxy radicals follow: bromo, chloro, fluoro, trifluoromethyl, iodo, lithio, alkyl, aryl, fused aryl, alkoxy, aroxy, cyano, nitro, hydroxy, amino, amido, ammonium, formyl, acyl, acetoxy, carbonyloxy, oxycarbonyl, phenylcyclohexyl, phenylbutenyl, tolyl, xylyl, para-ethylphenyl, pentafluorophenyl, phenoxy, hydroxymethyl, thio, sulfonato, sulfonyl, sulfinyl, silyl, phosphino, phosphinito, phosphonito, phosphito, phosphinato, phosphonato, sulfonamido, boro, borato, borinato, boronato, sulfinato, phosphonium, sulfonium, arsonato, and arsino.

The substituents can be ortho, meta, or para to the phosphorus atom. Up to five substituents can be present on each ring subject to the limitation on the number of carbons recited in the above generic formula. Subject to the same limitation, the aryl or aroxy radicals can be benzenoid, polyaromatic, heteroaromatic, or metal sandwiches, e.g., phenyl, thienyl, pyrryl, furyl, benzyl, pyridyl, phosphorinyl, imidizyl, naphthyl, anthracyl, phenanthryl, ferrocenyl, nickelocenyl, and chromocenyl.

Examples of alkyl and alkoxy radicals are as follows: methyl, diphenylphosphinomethyl, trifluoromethyl, ethyl, 2-cyanoethyl, 2-mercaptoethyl, 2-chloroethyl, 2-diphenylphosphinoethyl, 2-trimethylsilylethyl, 2-sulfonatoethyl, 1-propyl, 3-aminopropyl, 3-diphenylphosphinopropyl, 3-sulfonatopropyl, 1-butyl, 1-pentyl, 1-hexyl, 1-heptyl, 1-octyl, 1-nonyl, 1-decyl, t-butyl, 1,1-dimethyl-2-phenylethyl, 1,1-dimethylpropyl, 1,1,2-trimethylpropyl, 1,1-dimethylbutyl, 1,1-diethylpropyl, tricyclohexylmethyl, 1-adamantyl, cyclopropyl, cyclobutyl, 4-heptyl, cyclopentyl, cyclopropyl, methycyclopentyl, cyclohexyl, methylcyclohexyl, cycloheptyl, cyclooctyl, cyclododecyl, exo-norbornyl, endo-norbornyl, 2-bicyclo[2,2,2]octyl, 2-adamantyl, 2-propylheptyl, isobutyl, nopinyl, decahydronaphthyl, menthyl, neomenthyl, 2-ethylhexyl, neopentyl, isopropyl, 1-phenyl-2-propyl, 2-butyl, 2-pentyl, 3-pentyl, 2-hexyl, 3-hexyl, 2-heptyl, 3-heptyl, 4-heptyl, 2-octyl, 3-nonyl, and 5-decyl.

Examples of amino and amido groups follow: N,N-diethylamino, N,N-diphenylamino, N,N-dimethylamino, N,N-diisopropylamino, ethylamino, pyrryl, t-butylamino, anilino, succinamido, acetamido, and phthalimido.

A can be as described above; and M can be an alkali metal, an alkaline earth metal, an ammonium or phosphonium ion, or hydrogen.

Examples of useful ligands will be found in Table I.

Synthesis of ortho-phosphinosulfonates is accomplished by using the known reaction of a lithium benzenesulfonate with n-butyllithium to make ortholithiated lithium benzenesulfonate. Subsequent reaction with an organophosphorus halide gives the lithium salt of an ortho-organophosphorus sulfonate. These compounds can be converted to other salts by exchange reactions.

The synthesis of alkylene-phosphinosulfonates can be achieved, for example, by phosphide reaction on the sodium salt of 2-chloroethanesulfonic acid.

The molar ratio of metal salt to organophosphorus sulfonate is in the range of about 0.5 to one to about 5 to one and preferably in the range of about 0.5 to one to about 2.5 to one. The optimum ratio is considered to be about 2 to one. The catalyst is active at lower ratios; however, alpha-olefin selectivity is somewhat lower. By using two equivalents of phosphinosulfonate per nickel in aqueous solution, for example, the catalyst partitions in the aqueous phase. In this instance, it is believed that one phosphinosulfonate serves as a catalyst and the other serves as a solubilizing agent for the catalyst.

A sufficient amount of catalyst activator is incorporated into the complex to activate the catalyst. In some cases, the catalyst activator takes on the role of redox reagent, reducing or oxidizing the transition metal to an active oxidation state. Optimum amounts of catalyst activator in any particular system are determined by experimentation. The molar ratio of catalyst activator to metal salt is typically in the range of zero to about 5 to one and is preferably in the range of about 0.1 to one to about 3 to one. It is found that borohydride to nickel salt ratios of less than or equal to one to one give a very active catalyst in sulfolane when the nickel to ligand ratio is two. Ratios for this system ranging from 0.125 to one to one to one are most active with 0.25 to one being optimum. The ratio is also a function of the solvent used and the oxidation state of the transition metal.

The liquid phase reaction can be undertaken by dissolving catalyst in a solvent or suspending the catalyst in a liquid medium. The solvent or liquid medium should be inert to process components and apparatus under process conditions. Examples of solvents are ethanol, methanol, water, toluene, sulfolane, ethylene glycol, 1,4-butanediol, ethylene carbonate, and mixtures of the foregoing. Solvents which permit phase separation from oligomer product are preferred because product can then be isolated by decantation. Other methods of product separation such as distillation may require temperatures, which would be harmful to the catalyst. Examples of solvents which permit these separation are sulfolane, water, ethylene glycol, and 1,4-butanediol. It is noted that water shifts oligomer distribution to lower molecular weights. Some of the solvents, especially alcohols and diols, degrade with time under process conditions. Other suitable solvents can be found in U.S. Pat. Nos. 3,676,523 and 3,737,475, which are incorporated by reference herein.

One preferred solvent for ethylene oligomerization is water. Several advantages can be realized by water-soluble/oligomer insoluble catalysts: easy processing of product by substantially complete separation of catalyst from oligomers; increased alpha-olefin selectivity by minimizing olefin isomerization caused by catalyst/oligomer contact; ability to curtail oligomer chain length; and reduction of the problem of solvent degradation.

The most preferred solvent for ethylene oligomerization is sulfolane in which the catalyst is soluble, but the oligomer is not. The advantages of sulfolane follow: good partitioning of the organophosphorus sulfonate in the sulfolane phase; very high catalyst activity/productivity using appropriate generation ratios; good separation of catalyst from oligomers; increased alpha-olefin selectivity by minimizing olefin isomerization caused by catalyst/oligomer contact; lower catalyst usage and concentrations; lower catalyst activator usage; and reduction of the problem of solvent degradation. It should be noted that the sulfolane employed in the process can contain water and other impurities as long as catalyst activity is not impaired. Even when water content is sufficient to completely hydrolyze the more hydrolytically unstable catalyst activators, catalyst activity has been observed.

Nickel complexes of ortho-diphenylphosphino para-toluenesulfonate, ortho-diphenylphosphino-benzenesulfonate, and ortho-dicyclohexylphosphino-para-toluenesulfonate, when suspended in water or dissolved in water/ethanol cosolvent give oligomerization catalysts having good activity. These catalysts do not selectively partition in the aqueous phase, however, unless the ligand is present in excess over the nickel.

Optimum reaction conditions can be quite different for different ligand structures. For example, the more alkyl-phosphorus substituents in the phosphinosulfonate, the more stable the catalyst is at higher reaction temperatures. In some cases, the catalysts are more active and, therefore, lower concentrations of the catalyst are called for.

The oligomerization or cooligomerization process can be run at a temperature in the range of about 0 degrees C. to about 200 degrees C. Preferred temperatures are in the range of about 30° C. to about 140° C. It is suggested that a commercial unit be run in the range of about 60° C. to about 130° C.

Subject process can be run at pressures in the range of about atmospheric pressure to about 5000 psig. Preferred pressures are in the range of about 400 psig to about 2000 psig. These pressures are the pressures at which the ethylene or ethylene/propylene feed is introduced into the reactor, and at which the reactor is maintained. Pressure influences the performance of the catalyst. Experiments with ortho-diphenylphosphino-para-toluene-sulfonate/nickel catalyst are conducted at 70 degrees C. and pressures of 950 psig, 500 psig, and 200 psig in an ethanol solvent. At 200 psig, the olefin product is essentially limited to up to $C_{12}$ and alpha-olefin selectivities range from 25 to 78 percent by weight. At 500 psig, olefin product is essentially limited to no more than $C_{16}$, but alpha-olefin selectivities are only slightly lower than 950 psig. In contrast, experiments run in sulfolane are less responsive to changes in ethylene pressure and tend to produce higher molecular weight oligomer distribution.

Typical catalyst concentrations are in the range of about 10 ppm (parts per million) to about 1000 ppm of transition metal. The ppm is based on a million parts by weight of transition metal. Some of the more active catalysts give very high reaction rates at 40 ppm, however. A preferred range is about 0.1 ppm to about 1000 ppm (about 0.000002 mole per liter to about 0.02 mole per liter).

At high reaction rates, the reactions can be ethylene mass-transfer rate limited. At lower catalyst concentrations (100 ppm versus 1000 ppm Ni), the catalyst turnover frequency, which is defined as moles of ethylene per moles of transition metal per hour or gram ethylene per gram transition metal per hour, increases. Catalyst turnover frequency can be very high in sulfolane.

A typical catalyst activation follows: ligand, metal salt, and a tetraphenylborate catalyst activator are dissolved in a solvent and heated to reaction temperature prior to the introduction of ethylene. Unlike borohydrides, tetraphenylborate can be mixed with ligand and metal salt in the absence of ethylene without harming the catalyst significantly. With borohydride activator, a solution of ligand and metal salt is typically placed under 100 psig ethylene at about 0 to 50 degrees C. and a solution of borohydride introduced. Higher ethylene pressures would be better for catalyst generation. Preferred ethylene pressure is in the range of about atmospheric to about 500 psig. The catalyst generation temperature is in the range of about 0 degrees C. and about 50 degrees C. When mixtures of triphenylborane and borohydride are used as the activator, the triphenylborane can be added to the solution prior to or during the treatment with ethylene and borohydride at conditions within the same ranges. Triphenylborane enhances the activity of the catalyst while favoring the production of lighter alpha-olefins. The activity of a tetraphenylborate-based catalyst is higher than sodium borohydride/ethylene-based catalyst.

Subject catalysts are found to be very active. For example, a sodium salt of ortho-diphenylphosphino-para-toluenesulfonic acid/nickel chloride hexahydrate/sodium borohydride based catalyst gives good activity at ambient temperature. At 30 degrees C. 950 psi ethylene, and 1000 ppm nickel salt, a reaction rate of 0.5 gram-mole per liter per hour is noted. The products produced are about 96 to 99 percent by weight alpha-olefins in the $C_4$ to $C_{12}$ range. At higher temperatures, reaction rates are greater. In several tests, a minireactor is filled with oligomers within 0.5 to 2 hours. The discharged catalyst solutions contain 50 to 60 percent by weight of $C_4$ to $C_{20}$ oligomers and possess volumes close to 80 to 100 milliliters, the volume of the minireactor being 100 milliliters. Ethylene uptake slows as the reactor fills. Rates of over 15 gram-mole per liter per hour are often noted.

To determine catalyst stability, the reaction is monitored at low nickel concentrations (100 ppm Ni versus 1000 ppm Ni). Catalyst stability for the ortho-diphenylphosphino-para-toluene sulfonic acid based catalysts appears good at or below 80 degrees C. based on constant ethylene gas uptake.

In experiments with orthodiphenylphosphino-para-toluenesulfonic acid based catalysts, polyethylene formation is not observed when the reaction is conducted at temperatures even as low as ambient.

The lithium salt of ortho-diphenylphosphino-benzenesulfonic acid shows similar catalytic properties to the sodium salt of ortho-diphenylphosphino-para-toluenesulfonic acid.

Ligand cone angles, are noted, and phosphorus basicities influence catalyst properties. The sodium salt of ortho-dicyclohexylphosphino-p-toluenesulfonic acid gives a very active catalyst with nickel producing both ethylene oligomers and very low molecular weight polyethylene. Initial ethylene uptake rates with this ligand (1000 ppm Ni) are 190 gram-moles per liter per hour. Selectivity to granular polyethylene having an average molecular weight of about 900 is higher at 100 degrees C., while olefin oligomers form more readily at 130 degrees C. The ligand, being a dialkylarylphosphine, shows better stability at these elevated temperatures than triarylphosphine analogs. In contrast, the sodium salt of ortho-di-tert-butyl-phosphino-para-toluenesulfonic acid possesses lower activity, which suggests that the catalyst has a sharp response to ligand cone angle: the cone angle of the tert-butyl analog being slightly larger than the cyclohexyl analog. The large cone angle of ortho-dicyclohexylphosphino-para-toluenesulfonate appears to facilitate low molecular weight polyethylene formation. The phosphorus basicity of this ligand may also influence both the activity and selectivity of the catalyst.

When triphenylphosphine is added as an auxiliary ligand to an ortho-diphenylphosphino-para-toluenesulfonate/nickel catalyst, oligomer chain length is essentially curtailed to $C_8$ and alpha-olefin selectivity to under 50 percent, but polyethylene formation is not observed.

It will be understood by those skilled in the art that the operator of the process will have to make selections between the organo phosphorus sulfonate ligands, the transition metal compounds, the catalyst activators, concentrations, solvents, and reaction parameters in order to obtain the level of productivity sought.

In the event that the catalyst is discharged from the reactor while it is still active and recharged at a later time, activity is typically lost. If catalyst to be recharged is treated with additional catalyst activator, activity is restored. Preferably, treatment with transition metal compound and catalyst activator is used to restore activity.

The invention is illustrated by the following examples.

EXAMPLES 1 TO 55

Synthesis of the sodium salt of 2-diphenylphosphino-4-methylbenzenesulfonic acid:

Lithium-para-toluenesulfonate is prepared first. A solution of para-toluenesulfonic acid monohydrate (190 grams, 1.0 mole) in 400 milliliters of absolute ethanol is treated with lithium hydroxide monohydrate (42 grams, 1.0 mole). After stirring for one hour, the insolubles are filtered and the filtrate is concentrated to a white solid. The filtrate is treated with 400 milliliters of toluene and the resultant heterogeneous mixture is fitted with a condenser and refluxed for 8 hours (41 milliliters of water is azeotropically removed). The cooled mixture is filtered and the collected solids are pulverized and dried under vacuum (dry weight 163.5 grams).

The lithium salt of 2-diphenylphosphino-4-methylbenzenesulfonic acid is then prepared and converted to the sodium salt: lithium para-toluenesulfonate (8.9 grams, 50 millimoles) is suspended in 100 milliliters of dry tetrahydrofuran under a nitrogen atmosphere. The resultant suspension is cooled to 0 degrees C. and a solution of n-butyllithium in hexane (34 milliliters, 1.6 molar, 55 millimoles) is added at a dropwise rate creating an orange suspension. Thirty minutes later, diphenylchlorophosphine (11.3 grams, 51 millimoles) is added at a dropwise rate, which maintains the reaction temperature between 0 and 10 degrees C. resulting in a red reaction mixture. The reaction mixture is stripped of solvents to give a solid residue, treated with 200 milliliters of distilled water to give a turbid solution, and subsequently treated with 100 milliliters of saturated sodium chloride to precipitate the sodium salt. The resultant precipitate is washed twice with ether and dried under vacuum to a powder (12.81 gram).

Other phosphino-sulfonates can be prepared in the same manner by employing different lithium aromatic sulfonates and/or organophosphorus halides. One can stop at the lithium phosphino-sulfonate stage rather than converting it to the sodium salt. Lithium phosphino-sulfonates can be used as ligands without any formal purification other than stripping the reaction solvent. Treating the salts with strong acids can precipitate the "acid form" of the ligand. Reacting the "acid form" of the ligand with an appropriate metal hydroxide will, in turn, give metal phosphino-sulfonates useful as ligands.

Alkylenephosphino-sulfonates are prepared by the reaction of phosphides with haloalkanesulfonate salts. The lithium salt of 2-dicyclohexylphosphinoethanesulfonic acid is synthesized as follows: to a solution of dicyclohexylphosphine (10.6 grams, 53.4 millimoles) in dry tetrahydrofuran (100 milliliters) under a nitrogen atmosphere and cooled to minus 70 degrees C. is added n-butyllithium in hexane (1.6 molar, 31.25 milliliters, 50 millimoles). The resultant yellow mixture is allowed to warm to ambient temperature and the anhydrous sodium salt of 2-chloroethanesulfonic acid (9.25 grams, 55.5 millimoles) is added in 1 to 2 gram portions while the temperature is controlled between ambient and 41 degrees C. The resultant cloudy white solution is stripped of its solvent to give an off-white solid (18.3 grams).

The oligomerization of ethylene is carried out in a minireactor having a volume of 100 milliliters. The ethylene used is CP grade ethylene containing about 99.5 percent by weight ethylene. All solvents used in the minireactor are either distilled under nitrogen or thoroughly sparged with nitrogen prior to use.

In examples using nickel bis(1,5-cyclooctadiene), (written as Ni(COD)$_2$), a mixture of the solid nickel bis(1,5-cyclooctadiene) and ligand (1:1 mole ratio) is treated with the desired solvent (35 milliliters) and introduced into the minireactor within a matter of minutes. The minireactor is pressurized with 600 psig ethylene, heated to the desired temperature and, typically, the pressure is adjusted to 950 psig. it is found that aging of catalyst solutions for even a few hours prior to use resulted in lower catalytic activity.

In examples using nickel (II) chloride hexahydrate (or other metal salts), the ligand and nickel chloride mixture is treated with the solvent (35 milliliters) charged to the minireactor, and placed under 100 psig ethylene. A 0.5 molar solution of sodium borohydride in diglyme is introduced by pressure lock syringe at ambient temperature. The reactor is quickly pressurized to 600 psig ethylene, heated to the desired temperature, and, typically, the pressure is adjusted to 950 psig.

Reaction rates (ethylene uptake rates) are determined by monitoring the time required for 50 psi pressure drops measured continuously between 950 and 900 psig ethylene, assuming that ethylene behaves in the same way as an ideal gas under these reaction conditions (the reactor is repressurized to 950 psig after each rate measurement).

Upon completion of a run, the reactor is cooled to ambient temperature or below, vented to 200 psi, and the contents are dumped into a container chilled in dry ice/acetone. The total weight of the discharged catalyst is recorded and heptane internal standard is added. The products are analyzed on a Hewlett Packard 5880 gas chromatograph with a flame ionization detector using a J&W Scientific 30 meter×0.3 millimeter DB-1 fused silica capillary column. Temperature programming is used at the following rate: 0 degrees C. for one minute; then, a heating rate of 10 degrees C. per minute to 230 degrees C.; 230 degrees C. is maintained for 20 minutes (detector—300 degrees C., injector—250 degrees C.).

The alpha-olefins are readily separated from the corresponding branched and internal olefins by this method. The results are calculated as total weight percent oligomer relative to the weight of the reactor contents.

The letters SI appear under certain oligomers. SI means that there is solvent interference and, therefore, a weight percent cannot be obtained. When summations are made for total weight percent, the sums are low when solvent interference is reported.

Some catalysts produce oligomers beyond $C_{22}$. No attempt has been made to quantify the products.

The "product make by mass balance" does not always agree with "GC total $C_4$ to $C_{20}$ (grams)" (this refers to the total amount of $C_4$ to $C_{20}$ oligomers as determined by gas chromatographic analyses). "GC total $C_4$ to $C_{20}$ (grams)" is typically less because solvent interferes with oligomer analysis; butenes escape from the dumped catalyst prior to GC analysis; olefins greater than $C_{20}$ are produced; the minireactor has a flat bottom; and solvent rinses and discharged catalysts do not always dump quantitatively.

"GC total $C_4$ to $C_{20}$ (grams)" is divided by the run time in hours and the volume of the catalyst solution charged (usually 0.035 liter) to produce the "average reaction rate to $C_4$ to $C_{20}$-calculated". This value is typically greater (often 2 to 3 times) than the "ethylene uptake rate" and since it is based on actual observed product, it is more accurate than the indirect ethylene uptake method. Ethylene does not appear to behave like an ideal gas at high reaction pressures, e.g., 950 psig.

The structural formulae of useful ligands are set forth in Table I. The first fifteen structural formulae are each provided with a ligand number in parentheses. This number will be used to identify the ligand in Table II, i.e., the ligand used in each example.

Notes with respect to Table I:
Ph=phenyl
i-Pr=isopropyl
n-Bu=normal butyl

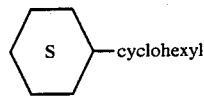

The conditions for each example are set forth in Table II and the results in Tables III and IV.

Notes with respect to Tables II, III, and IV:
1. Rates are given in gram-mole per liter per hour.
2. "OAc" is acetate.
3. "COD" is cyclooctadiene.
4. "GC" is gas chromatography. It is used to measure the amounts of the olefin products.
5. Parenthetical expressions in Table III are percentages by weight of normal alpha-olefin based on the total olefin product noted at the left of the parenthetical expression.
6. In examples 1 to 9, 0.10 millimoles of $NaBH_4$ in diglyme is added at 100 psig ethylene and 25° C.
7. In examples 10 to 15, 0.065 millimoles of $NaBH_4$ is added at 100 psig ethylene and 25° C.
8. In examples 16 to 18, 1.5 moles of catalyst activator $NaBH_4$ is added per mole of nickel compound.
9. In examples 19 to 25, $NaBH_4$ is added as a 0.5 molar solution in diglyme to the other catalyst components under 100 psig ethylene.
10. In examples 21, 22, 23, and 24, the exotherm is, respectively, 134.4° C., 179.7° C., 142.4° C., and 89.0° C. and the ratio of $BH_4^-/Ni^{++}$, 1:1, 1:2, 1:4, and 1:8. Examples having a $BH_4^-/Ni^{++}$ ratio between 1:1 and 1:8 result in extremely active catalysts. After injecting the sodium borohydride/diglyme solution into the reactor at around 35° C. and 100 psig ethylene, the reactor is further pressurized to about 750 psig and in examples 21 and 22, the reactor is heated. In examples 23 and 24 the reactor is not heated and the exotherm still occurs. As the reaction temperature approaches 60° C., the reaction rate shoots up resulting in a strong exotherm and very rapid ethylene pressure drop. The above temperatures are the maximum temperature of the reaction before cold air cooling of the minireactor catches the exotherm. These exotherms appear to be detrimental to catalyst stability/productivity and alpha-olefin selectivity, but the catalyst activity is very high.
11. In examples 26 to 32, the ligand/nickel molar ratio is 1 and the $NaBH_4$/nickel molar ratio is 1.5.
12. In example 33, the $LiBH_4$ is in the form of a 2.0 molar solution in tetrahydrofuran.
13. In example 35, the $NaBPh_4$ is added to the catalyst solution prior to charging to the minireactor.
14. In examples 57 and 58, there is an exotherm to 145° C. and 136.3° C., respectively. See Note 10 above.
15. In example 67, the $Et_3B$/hexane solution (25%) is added to the catalyst solution prior to charging to the minireactor.
16. In example 68, the $Et_3Al$/hexane solution (1.0M) is added to the catalyst solution under 100 psig ethylene.
17. In example 69, the $[Ph_3P]_2Cu(I)BH_4$ is added to the catalyst solution prior to charging to the minireactor.
18. In example 70, the $BH_3$/tetrahydrofuran (1.0M) solution is added to the catalyst solution under 100 psig ethylene.
19. In example 71, the $LiAlH_4$/tetrahydrofuran (1.0M) solution is added to the catalyst solution under 100 psig ethylene.
20. In example 72, the $i-Bu_2AlH$/hexane (1.0M) solution is added to the catalyst solution under 100 psig ethylene.

TABLE I

| ligand # | ligand |
|---|---|
| (1) | $SO_3Na$, $PPh_2$, $CH_3$ (benzene ring) |
| (2) | $SO_3Li$, $PPh_2$ (benzene ring) |
| (3) | $SO_3Li$, P(Ph)(S-cyclohexyl) (benzene ring) |
| (4) | $SO_3Li$, $P(i-Pr)_2$ (benzene ring) |
| (5) | $SO_3Li$, $P(CH_3)_2$ (benzene ring) |

TABLE I-continued

| ligand # | ligand |
|---|---|
| (6) | 2-(SO$_3$Li)-C$_6$H$_4$-P(Ph)(n-Bu) |
| (7) | (Cy)$_2$PCH$_2$CH$_2$SO$_3$Na |
| (8) | [2-(SO$_3$Li)-4-(CH$_3$)-C$_6$H$_3$]$_3$P |
| (9) | Ph$_2$PCH$_2$CH$_2$SO$_3$Na |
| (10) | 2-(SO$_3$Li)-C$_6$H$_4$-P(Ph)(Cy) |
| (11) | 2-(SO$_3$Na)-4-(CH$_3$)-C$_6$H$_3$-P(Cy)$_2$ |
| (12) | H$^+$ [2-(SO$_3^-$)-C$_6$H$_4$-PPh$_2$] |
| (13) | P[OC$_6$H$_2$(t-Bu)(CH$_3$)-CH$_2$-C$_6$H$_2$(CH$_3$)(t-Bu)O][2-(SO$_3$Li)-4-(CH$_3$)-C$_6$H$_3$] |
| (14) | 2-(SO$_3$Li)-4-(CH$_3$)-C$_6$H$_3$-P(Ph)(i-Pr) |
| (15) | 2-(SO$_3$Li)-5-(CH$_3$)-C$_6$H$_3$-P(C$_6$F$_5$)$_2$ |
| (16) | 1-(SO$_3$Li)-2-(PPh$_2$)-naphthalene and/or 1-(PPh$_2$)-8-(SO$_3$Li)-naphthalene |
| (17) | 2-(SO$_3$K)-C$_6$H$_4$-PPh$_2$ |
| (18) | 2-(SO$_3$[(CH$_3$)$_4$N])-C$_6$H$_4$-PPh$_2$ |
| (19) | 2-(SO$_3$Li)-C$_6$H$_4$-PEt$_2$ |
| (20) | P[OC$_6$H$_2$(t-Bu)(CH$_3$)-CH$_2$-C$_6$H$_2$(CH$_3$)(t-Bu)O](OCHSO$_3$Li)(2-pyridyl) |
| (21) | 2-(SO$_2$N(CH$_3$)Li)-4-(CH$_3$)-C$_6$H$_3$-PPh$_2$ |

TABLE I-continued

| ligand # | ligand |
|---|---|
| (22) | 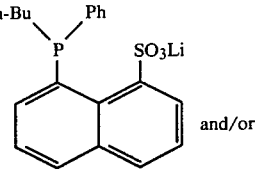 and/or 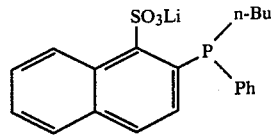 |
| (23) | 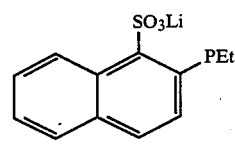 and/or 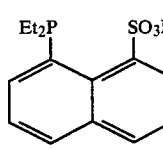 |
| (24) | 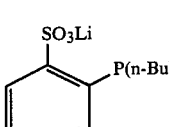 |

An example of a bridging aromatic ring system having a trivalent phosphorous atom and an SO$_3$M group, each located on a different aromatic ring in the system at substituent positions adjacent to one another follows:

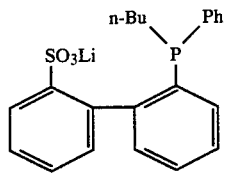

An example of a fused aromatic ring system having a trivalent phosphorous atom and an SO$_3$M group, each located on a different aromatic ring in the system at a substituent positions adjacent to one another follows:

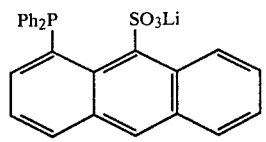

An example of an aromatic compound having a trivalent phosphorus atom connected through a methylene group to a first position on a benzene ring and an SO$_3$M group connected through a methylene group to a second position on the benzene ring ortho to the first position:

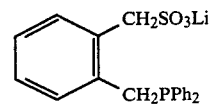

Examples of an aromatic ring compound, other than a benzene ring compound, and a heteroaromatic ring compound where the rings have a trivalent phosphorus atom and an SO$_3$M group located at substituent positions adjacent to one another on the ring:

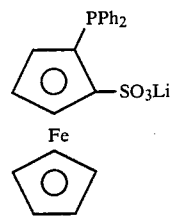

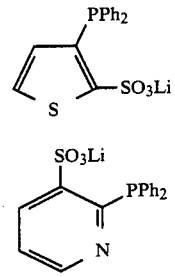

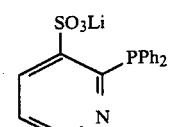

TABLE II

| Example | Ligand | Millimoles | Transition Metal Compound | Millimoles | Catalyst Activator | Millimoles | Solvent | Milliliters | Run Temperature (°C.) | Run Pressure (psig) | Ethylene Uptake Rate (gram-mol/L/hr) |
|---|---|---|---|---|---|---|---|---|---|---|---|
| 1 | (1) | 0.065 | NiCl$_2$.6H$_2$O | 0.065 | NaBH$_4$ | 0.100 | ethanol | 35 | 80 | 950 | 8.6 to 3.5 |
| 2 | (1) | 0.065 | NiSO$_4$.6H$_2$O | 0.065 | NaBH$_4$ | 0.100 | ethanol | 35 | 80 | 950 | — |
| 3 | (1) | 0.065 | NiBr$_2$.xH$_2$O | 0.050 | NaBH$_4$ | 0.100 | ethanol | 35 | 80 | 950 | 0.42 |
| 4 | (1) | 0.065 | Ni(II)acetyl-acetonate | 0.065 | NaBH$_4$ | 0.100 | ethanol | 35 | 80 | 950 | — |
| 5 | (1) | 0.065 | NiBr$_2$.6H$_2$O | 0.065 | NaBH$_4$ | 0.100 | ethanol | 35 | 80 | 950 | 1.4 to 1.3 |
| 6 | (1) | 0.065 | Ni(NO$_3$)$_2$.6H$_2$O | 0.065 | NaBH$_4$ | 0.100 | ethanol | 35 | 80 | 950 | — |
| 7 | (1) | 0.065 | Ni(OAc)$_2$.4H$_2$O | 0.065 | NaBH$_4$ | 0.100 | ethanol | 35 | 80 | 950 | 0.40 |
| 8 | (1) | 0.065 | NiCl$_2$.dimethoxyethane | 0.065 | NaBH$_4$ | 0.100 | ethanol | 35 | 80 | 950 | — |
| 9 | (1) | 0.065 | NiCl$_2$.6H$_2$O + 1.0 mmol LiCl | 0.065 | NaBH$_4$ | 0.100 | ethanol | 35 | 80 | 950 | — |
| 10 | (1) | 0.065 | Ni(OH)$_2$ | 0.130 | NaBH$_4$ | 0.065 | ethanol | 35 | 80 | 950 | — |
| 11 | (1) | 0.065 | hexamminickel(II) chloride | 0.130 | NaBH$_4$ | 0.065 | ethanol | 35 | 80 | 950 | — |
| 12 | (1) | 0.065 | NiCl$_2$ (anhydrous) | 0.130 | NaBH$_4$ | 0.065 | ethanol | 35 | 80 | 950 | — |
| 13 | (1) | 0.065 | Ni benzoate | 0.130 | NaBH$_4$ | 0.065 | ethanol | 35 | 80 | 950 | — |
| 14 | (1) | 0.065 | nickel flouride. 4H$_2$O | 0.130 | NaBH$_4$ | 0.065 | ethanol | 35 | 80 | 950 | — |
| 15 | (1) | 0.065 | NiCl$_2$.6H$_2$O | 0.130 | NaBH$_4$ | 0.065 | ethanol | 35 | 80 | 950 | 3.2 to 2.4 |
| 16 | (1) | 0.1625 | Ni(BF$_4$)$_2$.6H$_2$O | — | NaBH$_4$ | — | sulfolane | 35 | 80 | 900 to 950 | 8.65 to 2.33 |
| 17 | (1) | 0.1625 | Ni(BF$_4$)$_2$.6H$_2$O | — | NaBH$_4$ | — | sulfolane | 35 | 80 | 900 to 950 | 1.65 to 0.87 |
| 18 | (1) | 0.1625 | Ni(BF$_4$)$_2$.6H$_2$O | — | NaBH$_4$ | — | sulfolane | 35 | 80 | 900 to 950 | 1.39 to 1.23 |
| 19 | (1) | 0.1625 | Ni(BF$_4$)$_2$.6H$_2$O | 0.325 | NaBH$_4$ | — | sulfolane | 35 | 80 | 900 to 950 | 3.1 to 1.1 |
| 20 | (1) | 0.1625 | Ni(BF$_4$)$_2$.6H$_2$O | 0.325 | NaBH$_4$ | — | sulfolane | 35 | 80 | 900 to 950 | 8.7 to 2.3 |
| 21 | (1) | 0.1625 | Ni(BF$_4$)$_2$.6H$_2$O | 0.325 | NaBH$_4$ | — | sulfolane | 35 | 80 | 900 to 950 | 38.5 to 5.1 |
| 22 | (1) | 0.1625 | Ni(BF$_4$)$_2$.6H$_2$O | 0.325 | NaBH$_4$ | — | sulfolane | 35 | 80 | 900 to 950 | 6.1 to 5.1 |
| 23 | (1) | 0.1625 | Ni(BF$_4$)$_2$.6H$_2$O | 0.325 | NaBH$_4$ | — | sulfolane | 35 | 80 | 900 to 950 | 92.6 to 3.6 |
| 24 | (1) | 0.1625 | Ni(BF$_4$)$_2$.6H$_2$O | 0.325 | NaBH$_4$ | — | sulfolane | 35 | 80 | 900 to 950 | 34.1 to 4.9 |
| 25 | (1) | 0.1625 | Ni(BF$_4$)$_2$.6H$_2$O | 0.325 | NaBH$_4$ | — | sulfolane | 35 | 80 | 900 to 950 | 11.1 to 2.2 |
| 26 | (1) | — | NiCl$_2$.6H$_2$O | 0.195 | NaBH$_4$ | — | methanol | 35 | 80 | 900 to 950 | 2.25 to 1.32 |
| 27 | (1) | — | NiCl$_2$.6H$_2$O | 0.192 | NaBH$_4$ | — | ethanol/H$_2$O | 29.75/5.25 | 80 | 900 to 950 | 3.7 to 1.9 |
| 28 | (1) | — | NiCl$_2$.6H$_2$o | 0.195 | NaBH$_4$ | — | sulfolane | 35 | 80 | 900 to 950 | 2.49 to 1.84 |
| 29 | (1) | — | Ni(BF$_4$)$_2$.6H$_2$O | 0.65 | NaBH$_4$ | — | ethylene glycol | 35 | 80 | 900 to 950 | 11.03 to 1.43 |
| 30 | (1) | — | Ni(BF$_4$)$_2$.6H$_2$O | 0.65 | NaBH$_4$ | — | ethylene carbonate | 35 | 80 | 900 to 950 | 10.6 to 2.11 |

TABLE II-continued

| Example | Ligand | Millimoles | Transition Metal Compound | Millimoles | Catalyst Activator | Millimoles | Solvent | Milliliters | Run Temperature (°C) | Run Pressure (psig) | Ethylene Uptake Rate (gram-mol/L/hr) |
|---|---|---|---|---|---|---|---|---|---|---|---|
| 31 | (1) | | $NiCl_2 \cdot 6H_2O$ | 0.65 | $NaBH_4$ | — | 1,4-butane-diol | 35 | 80 | 900 to 950 | 2.81 to 4.11 |
| 32 | (1) | | $Ni(BF_4)_2 \cdot 6H_2O$ | 0.065 | $NaBH_4$ | — | sulfolane | 35 | 80 | 900 to 950 | 1.53 to 1.07 |
| 33 | (2) | | $NiCl_2 \cdot 6H_2O$ | 0.65 | $LiBH_4$ | 1.0 | ethanol | — | 80 | 900 to 950 | 5.23 to 2.24 |
| 34 | (2) | | $NiCl_2 \cdot 6H_2O$ | 0.65 | $LiBPh_4$ | 1.0 | ethanol | — | 80 | 900 to 950 | 25.4 to 5.66 |
| 35 | (2) | | $NiCl_2 \cdot 6H_2O$ | 0.65 | $NaBPh_4$ | 1.0 | ethanol | — | 80 | 900 to 950 | 6.47 to 46.9 to 12.0 |
| 36 | (2) | | $NiCl_2 \cdot 6H_2O$ | 0.65 | $NaBH_4/Ph_3B$ | 1.0/0.95 | ethanol | — | 80 | 900 to 950 | 44.1 to 8.67 |
| 37 | (3) | | $CrCl_3 \cdot 6H_2O$ | 0.65 | $NaBPh_4$ | 2.0 | sulfolane | 35 | 100 | 900 to 950 | 1.20 to 3.27 |
| 38 | (3) | | $CrCl_3 \cdot 6H_2O$ | 0.65 | $NaBPh_4$ | 2.0 | sulfolane | 35 | 100 | 900 to 950 | 9.77 to 2.55 |
| 39 | (3) | | $CrCl_3 \cdot 6H_2O$ | 0.65 | $NaBPh_4$ | 2.0 | sulfolane | 35 | 130 | 900 to 950 | 0.41 to 0.67 |
| 40 | (3) | | $CrCl_3 \cdot 6H_2O$ | 0.65 | $NaBPh_4$ | 2.0 | sulfolane | 35 | 100 | 900 to 950 | 2.64 to 1.96 |
| 41 | (3) | | $CoCl_2 \cdot 6H_2O$ | 0.65 | $NaBPh_4$ | 1.0 | sulfolane | 35 | 100 | 900 to 950 | — |
| 42 | (3) | | $CuCl_2 \cdot 6H_2O$ | 0.65 | $NaBPh_4$ | 1.0 | sulfolane | 35 | 100 | 900 to 950 | — |
| 43 | (4) | | $CrCl_3 \cdot 6H_2O$ | 0.65 | $NaBPh_4$ | 1.0 | sulfolane | 35 | 100 | 900 to 950 | — |
| 44 | (5) | 0.65 | $NiCl_2 \cdot 6H_2O$ | 0.65 | $NaBH_4$ | 1.0 | ethanol | — | 100 to 120 | — | 0.46 (at 120° C.) |
| 45 | (6) | 0.65 | $NiCl_2 \cdot 6H_2O$ | 0.65 | $NaBH_4$ | 1.0 | ethanol | — | 80 | — | 7.90 to 2.13 |
| 46 | (7) | 0.65 | $NiCl_2 \cdot 6H_2O$ | 0.65 | $NaBH_4$ | 1.0 | ethanol | — | 100 | — | 10.4 to 2.95 |
| 47 | (8) | 0.65 | $NiCl_2 \cdot 6H_2O$ | 0.65 | $NaBH_4$ | 1.0 | ethanol | — | 80 | — | — |
| 48 | (9) | 0.65 | $NiCl_2 \cdot 6H_2O$ | 0.65 | $NaBH_4$ | 1.0 | ethanol | — | 100 | — | — |
| 49 | (10) | 0.65 | $Ni(BF_4)_2 \cdot 6H_2O$ | 0.65 | $NaBPh_4$ | 1.0 | sulfolane | — | 80 | — | 35.7 to 3.16 |
| 50 | (4) | 0.1625 | $Ni(BF_4)_2 \cdot 6H_2O$ | 0.1625 | $NaBPh_4$ | 0.1625 | sulfolane | — | 110 | — | 131.0 to 8.67 |
| 51 | (11) | 0.065 | $Ni(BF_4)_2 \cdot 6H_2O$ | 0.065 | $NaBPh_4$ | 0.10 | sulfolane | — | 110 to 15 | — | 60.8 to 9.1 |
| 52 | (12) | 0.65 | $Ni(COD)_2$ | 0.65 | — | — | sulfolane | — | 80 | — | 1.59 to 1.01 |
| 53 | (13) | 0.65 | $NiCl_2 \cdot 6H_2O$ | 0.65 | $NaBH_4$ | 0.25 | ethanol | — | 50 | — | 0.66 |
| 54 | (14) | 0.65 | $NiCl_2 \cdot 6H_2O$ | 0.65 | $NaBPh_4$ | 1.0 | sulfolane | — | 100 | — | 4.38 to 21.96 |
| 55 | (15) | 0.1625 | $Ni(BF_4)_2 \cdot 6H_2O$ | 0.325 | $NaBPh_4$ | 0.4857 | sulfolane | 35 | 80 | 950 | 1.197 to 0.537 |
| 56 | (16) | 0.065 | $Ni(tosylate)_2 \cdot 6H_2O$ | 0.130 | $NaBH_4$ | 0.065 | sulfolane | 35 | 80 | 950 | 49.2 to 4.3 |
| 57 | (17) | 0.065 | $Ni(tosylate)_2 \cdot 6H_2O$ | 0.130 | $NaBH_4$ | 0.065 | sulfolane | 35 | 80 | 950 | 17.62 to 7.05 |
| 58 | (18) | 0.065 | $Ni(tosylate)_2 \cdot 6H_2O$ | 0.130 | $NaBH_4$ | 0.065 | sulfolane | 35 | 80 | — | 13.73 to 8.72 |
| 59 | (19) | 0.065 | $Ni(tosylate)_2 \cdot 6H_2O$ | 0.130 | $NaBH_4$ | 0.065 | sulfolane | 35 | 80 | — | 18.98 to 2.04 |
| 60 | (20) | 0.131 | $Ni(BF_4)_2 \cdot 6H_2O$ | 0.325 | $NaBPh_4$ | 0.4857 | sulfolane | 35 | 100 | — | 0.18 |
| 61 | (7) | 0.065 | $Ni(BF_4)_2 \cdot 6H_2O$ | 0.130 | $NaBH_4$ | 0.065 | sulfolane | 35 | 80 | — | 16.18 to 7.29 |

TABLE II-continued

| Example | Ligand | Millimoles | Transition Metal Compound | Millimoles | Catalyst Activator | Millimoles | Solvent | Milliliters | Run Temperature (°C.) | Run Pressure (psig) | Ethylene Uptake Rate (gram-mol/L/hr) |
|---|---|---|---|---|---|---|---|---|---|---|---|
| 62 | (21) | 0.065 | Ni(BF$_4$)$_2$·6H$_2$O | 0.130 | NaBH$_4$ | 0.065 | sulfolane | 35 | 80 to 100 | — | — |
| 63 | (22) | 0.065 | Ni(BF$_4$)$_2$·6H$_2$O | 0.130 | NaBH$_4$ | 0.065 | sulfolane | 35 | 80 | — | 34.74 to 8.24 |
| 64 | (23) | 0.065 | Ni(BF$_4$)$_2$·6H$_2$O | 0.130 | NaBH$_4$ | 0.065 | sulfolane | 35 | 80 | — | 60.66 to 4.74 |
| 65 | (24) | 0.065 | Ni(BF$_4$)$_2$·6H$_2$O | 0.130 | NaBH$_4$ | 0.065 | sulfolane | 35 | 80 | — | 15.80 to 0.86 |
| 66 | (12) | 0.065 | [Ph$_3$P]$_2$Ni(CO)$_2$ | 0.130 | — | — | sulfolane | 35 | 80 | — | — |
| 67 | (22) | 0.065 | Ni(BF$_4$)$_2$·6H$_2$O | 0.130 | Et$_3$B | 0.26 | sulfolane | 35 | 80 | — | 11.58 to 2.79 |
| 68 | (22) | 0.016 | Ni(BF$_4$)$_2$·6H$_2$O | 0.033 | Et$_3$Al | 0.065 | sulfolane | 35 | 80 | — | 16.05 to 2.99 |
| 69 | (22) | 0.065 | Ni(BF$_4$)$_2$·6H$_2$O | 0.130 | [Ph$_3$P]$_2$Cu(I)BH$_4$ | 0.130 | sulfolane | 35 | 80 | — | 13.73 to 1.56 |
| 70 | (22) | 0.065 | Ni(BF$_4$)$_2$·6H$_2$O | 0.130 | BH$_3$·THF | 0.26 | sulfolane | 35 | 80 | — | 6.41 to 4.24 |
| 71 | (22) | 0.065 | Ni(BF$_4$)$_2$·6H$_2$O | 0.130 | LiAlH$_4$ | 0.130 | sulfolane | 35 | 80 | — | 4.77 to 3.75 |
| 72 | (22) | 0.65 | Ni(BF$_4$)$_2$·6H$_2$O | 0.130 | i-Bu$_2$AlH | 0.26 | sulfolane | 35 | 80 | — | 15.35 to 2.67 |

TABLE III

| Example | Phase | OLEFIN (WT. %) (ALPHA-OLEFIN WT. % OF OLEFIN) | | | | | | | | |
|---|---|---|---|---|---|---|---|---|---|---|
| | | $C_4$ | $C_6$ | $C_8$ | $C_{10}$ | $C_{12}$ | $C_{14}$ | $C_{16}$ | $C_{18}$ | $C_{20}$ | $C_{22}$ |
| 1 | Single | 6.874 (96) | 11.195 (95) | 7.520 (97) | 4.500 (95) | 2.450 (92) | 1.190 (89) | 0.557 (88) | 0.248 (100) | 0.117 (100) | — |
| 2 | Single | 0.096 (96) | 0.221 (99) | — (99) | 0.131 (100) | 0.084 (100) | 0.052 (100) | 0.031 (100) | 0.018 (100) | 0.013 (100) | — |
| 3 | Single | 0.908 (97) | 1.725 (98) | 1.234 (99) | 0.778 (99) | 0.471 (97) | 0.260 (100) | 0.143 (100) | 0.081 (100) | 0.042 (100) | — |
| 4 | Single | 0.62 (97) | 0.109 (97) | 0.073 (100) | 0.0464 (100) | 0.028 (100) | 0.017 (100) | 0.010 (100) | 0.006 (100) | — | — |
| 5 | Single | 2.259 (94) | 3.742 (96) | 2.443 (98) | 1.43 (98) | 0.821 (95) | 0.435 (100) | 0.202 (100) | 0.098 (100) | 0.037 (100) | — |
| 6 | Single | 0.136 (96) | 0.298 (96) | 0.231 (99) | 0.156 (100) | 0.099 (100) | 0.060 (100) | 0.037 (100) | 0.022 (100) | 0.012 (100) | — |
| 7 | Single | 0.484 (98) | 1.039 (96) | 0.782 (99) | 0.526 (100) | 0.337 (100) | 0.207 (100) | 0.126 (100) | 0.078 (100) | 0.044 (100) | — |
| 8 | Single | 0.009 (100) | 0.019 (100) | 0.017 (100) | 0.014 (100) | 0.009 (100) | 0.007 (100) | 0.005 (100) | — | 0.004 (100) | — |
| 9 | Single | 0.377 (96) | 0.700 (97) | 0.492 (99) | 0.304 (99) | 0.179 (96) | 0.091 (100) | 0.047 (100) | 0.027 (100) | 0.012 (100) | — |
| 10 | Single | — | 0.005 (100) | 0.165 (100) | 0.284 (100) | 0.302 (100) | 0.254 (100) | 0.201 (100) | 0.173 (100) | 0.137 (100) | — |
| 11 | Single | 0.443 (75) | 0.260 (79) | 0.075 (90) | 0.034 (100) | 0.029 (100) | 0.025 (100) | 0.023 (100) | 0.021 (100) | 0.020 (100) | — |
| 12 | Single | 0.104 (100) | 0.220 (98) | 0.165 (100) | 0.096 (100) | 0.057 (100) | 0.036 (100) | 0.026 (100) | 0.016 (100) | — | — |
| 13 | Single | — | — | — | 0.010 (100) | 0.014 (100) | 0.016 (100) | 0.018 (100) | 0.016 (100) | — | — |
| 14 | Single | — | — | — | — | 0.019 (100) | 0.028 (100) | 0.029 (100) | 0.026 (100) | 0.020 (100) | — |
| 15 | Single | 6.297 (97) | 8.741 (96) | 6.780 (98) | 4.336 (96) | 2.642 (98) | 1.491 (100) | 0.801 (100) | 0.460 (100) | 0.205 (100) | — |
| 16 | Top | 2.591 (95) | 6.085 (94) | 4.782 (96) | 3.247 (97) | 2.148 (93) | 1.353 (91) | 0.878 (96) | 0.627 (83) | 0.342 (89) | — |
| | Bottom | 1.284 (74) | 1.330 (84) | 0.578 (85) | 0.210 (100) | SI | 0.043 (100) | 0.020 (100) | 0.014 (100) | — | — |
| | Total | 3.875 | 7.415 | 5.36 | 3.457 | 2.148 | 1.396 | 0.898 | 0.641 | 0.342 | — |
| 17 | Top | 0.056 (93) | 0.686 (96) | 0.916 (97) | 0.782 (99) | 0.567 (94) | 0.353 (92) | 0.212 (86) | 0.134 (82) | 0.072 (86) | — |
| | Bottom | 0.551 (90) | 1.125 (100) | 0.594 (100) | 0.228 (100) | SI | | | | | |
| | Total | 0.607 | 1.81 | 1.51 | 1.01 | 0.567 | 0.353 | 0.212 | 0.134 | 0.072 | — |
| 18 | Top | 0.053 (95) | 0.569 (96) | 0.729 (97) | 0.599 (99) | 0.441 (94) | 0.278 (91) | 0.167 (86) | 0.109 (81) | 0.058 (86) | — |
| | Bottom | 0.837 (79) | 1.612 (98) | 1.398 (97) | 0.712 (100) | SI | 0.642 (100) | 0.116 (100) | 0.069 (100) | 0.039 (100) | 0.102 (95) |
| | Total | 0.890 | 2.181 | 2.127 | 1.311 | 0.441 | 0.92 | 0.283 | 0.178 | 0.09 | 0.102 |
| 19 | Top | 0.115 (94) | 0.692 (94) | 0.905 (95) | 0.742 (97) | 0.597 (91) | 0.432 (89) | 0.309 (84) | 0.224 (84) | 0.151 (77) | — |
| | Bottom | 0.460 (92) | 0.770 (96) | 0.416 (100) | 0.186 (100) | 0.087 (100) | 0.047 (100) | 0.041 (100) | 0.033 (100) | SI | 0.102 |
| | Total | 0.575 | 1.462 | 1.321 | 0.928 | 0.684 | 0.479 | 0.35 | 0.257 | 0.151 | — |
| 20 | Top | 2.591 (95) | 6.085 (94) | 4.782 (96) | 3.247 (97) | 2.148 (93) | 1.353 (91) | 0.878 (96) | 0.627 (83) | 0.342 (89) | — |
| | Bottom | 1.284 (74) | 1.330 (84) | 0.578 (85) | 0.210 (100) | SI | 0.043 (100) | 0.020 (100) | 0.014 (100) | — | — |
| | Total | 3.875 | 7.415 | 5.36 | 3.457 | 2.148 | 1.396 | 0.898 | 0.641 | 0.342 | — |
| 21 | Top | 3.687 (91) | 7.145 (86) | 6.708 (90) | 5.212 (92) | 4.378 (87) | 3.365 (85) | 2.642 (80) | 2.258 (79) | 1.636 (74) | 1.135 (67) |
| | Bottom | 0.653 (46) | 0.493 (44) | 0.204 (62) | 0.058 (100) | SI | 0.022 (100) | — | — | SI | — |
| | Total | 4.34 | 7.638 | 6.912 | 5.27 | 4.378 | 3.387 | 2.642 | 2.258 | 1.636 | 1.135 |
| 22 | Top | 2.262 (80) | 4.215 (75) | 4.069 (82) | 3.184 (89) | 3.079 (77) | 2.511 (77) | 2.037 (73) | 1.939 (65) | 1.422 (68) | 1.035 (92) |
| | Bottom | 0.545 (75) | 0.481 (71) | 0.239 (83) | 0.089 (100) | SI | 0.032 (100) | 0.024 (100) | 0.025 (100) | — | — |
| | Total | 2.807 | 4.696 | 4.308 | 3.273 | 3.079 | 2.543 | 2.061 | 1.964 | 1.442 | 1.035 |
| 23 | Top | 5.318 (83) | 6.755 (74) | 6.153 (85) | 4.974 (87) | 4.435 (85) | 3.741 (80) | 2.977 (76) | 2.648 (71) | 1.904 (77) | 1.588 (93) |
| | Bottom | 0.651 (55) | 0.340 (47) | 0.119 (71) | 0.029 (100) | 0.014 (100) | — | — | — | SI | — |
| | Total | 5.969 | 7.095 | 6.272 | 5.00 | 4.449 | 3.741 | 2.977 | 2.648 | 1.904 | 1.588 |
| 24 | Top | 6.671 (94) | 6.567 (89) | 5.903 (93) | 4.932 (96) | 4.266 (93) | 3.592 (88) | 2.942 (83) | 2.530 (84) | 2.121 (69) | 1.301 (96) |
| | Bottom | 0.756 (94) | 0.351 (94) | 0.159 (100) | 0.069 (100) | 0.038 (100) | 0.022 (100) | — | — | SI | — |
| | Total | 7.427 | 6.918 | 6.062 | 5.001 | 4.340 | 3.612 | 2.942 | 2.530 | 2.121 | 1.301 |
| 25 | Top | 1.287 (95) | 2.405 (92) | 2.750 (94) | 2.458 (97) | 2.258 (92) | 1.856 (91) | 1.523 (84) | 1.223 (85) | 0.864 (84) | 0.739 (96) |
| | Bottom | 0.438 (95) | 0.289 (100) | 0.135 (100) | 0.066 (100) | 0.033 (100) | — | — | — | — | — |
| | Total | 1.725 | 2.694 | 2.885 | 2.524 | 2.291 | 1.856 | 1.523 | 1.223 | 0.864 | 0.739 |
| 26 | Single | SI | 3.844 (93) | 1.484 (96) | 0.493 (94) | 0.115 (96) | 0.046 (100) | 0.024 (100) | 0.009 (100) | — | — |
| 27 | Single | 3.775 (93) | 4.842 (93) | 1.923 (96) | 0.676 (91) | 0.230 (90) | 0.069 (100) | 0.026 (100) | 0.223 (84) | 0.151 (86) | — |
| 28 | Top | 0.073 (87) | 0.791 (95) | 1.005 (96) | 0.772 (98) | 0.583 (93) | 0.412 (91) | 0.297 (86) | 0.019 (100) | — | — |
| | Bottom | 0.639 (94) | 0.999 (94) | 0.526 (97) | 0.746 (100) | 0.226 (100) | 0.037 (100) | 0.016 (100) | 0.242 | 0.154 | — |
| | Total | 0.712 | 1.79 | 1.531 | 1.518 | 0.809 | 0.449 | 0.313 | 0.046 (86) | 0.031 (89) | — |
| 29 | Top | 0.214 (98) | 3.706 (93) | 1.173 (96) | 0.313 (90) | 0.109 (89) | 0.068 (89) | 0.055 (85) | | | — |

TABLE III-continued

| Example | Phase | OLEFIN (WT. %) (ALPHA-OLEFIN WT. % OF OLEFIN) | | | | | | | | | |
|---|---|---|---|---|---|---|---|---|---|---|---|
| | | $C_4$ | $C_6$ | $C_8$ | $C_{10}$ | $C_{12}$ | $C_{14}$ | $C_{16}$ | $C_{18}$ | $C_{20}$ | $C_{22}$ |
| 30 | Bottom | 0.139 (69) | 0.625 (89) | SI | 0.126 (100) | SI | — | 0.010 (100) | 0.004 (100) | — | — |
| | Total | 0.353 | 4.331 | 1.173 | 0.439 | 0.109 | 0.068 | 0.065 | 0.050 | 0.031 | — |
| 31 | Single | 0.115 (61) | 0.472 (89) | 0.169 (88) | 0.012 (84) | 0.030 (100) | 0.015 (92) | 0.012 (100) | — | 0.032 (90) | — |
| 32 | Single | 2.151 (88) | 3.080 (89) | 1.854 (94) | SI | 0.509 (93) | 0.252 (92) | 0.127 (87) | 0.032 (79) | 0.026 (100) | — |
| | Top | 0.009 (92) | 1.082 (94) | 1.055 (96) | 0.678 (99) | 0.393 (98) | 0.202 (97) | 0.101 (100) | 0.052 (100) | 0.047 (100) | — |
| | Bottom | 0.058 (87) | 1.559 (94) | 1.067 (96) | 0.573 (99) | — | 0.179 (97) | 0.106 (100) | 0.072 (100) | — | — |
| | Total | 0.067 | 2.641 | 2.122 | 1.251 | 0.393 | 0.381 | 0.207 | 0.124 | 0.073 | — |
| 33 | Single | 4.326 (95) | SI | 4.881 (96) | 3.004 (96) | 1.694 (93) | 0.842 (91) | 3.41 (96) | 0.146 (100) | 0.058 (100) | — |
| 34 | Single | 9.737 (95) | 13.397 (92) | 8.566 (94) | 4.862 (93) | 2.642 (88) | 1.247 (83) | 0.548 (81) | 0.190 (100) | 0.079 (100) | — |
| 35 | Single | 10.723 (85) | 12.714 (80) | 8.780 (86) | 5.325 (86) | 3.500 (77) | 2.143 (70) | 1.364 (65) | 0.997 (57) | 0.539 (70) | — |
| 36 | Single | 14.454 (96) | 16.915 (93) | 8.111 (94) | 3.407 (90) | 1.344 (85) | 0.533 (78) | 0.175 (89) | 0.059 (100) | 0.019 (100) | — |
| 37 | Top | 0.273 (93) | 1.253 (94) | 1.325 (96) | 1.114 (97) | 0.896 (94) | 0.666 (91) | 0.463 (88) | 0.348 (83) | 0.214 (87) | — |
| | Bottom | 0.636 (96) | 0.770 (100) | 0.411 (100) | 0.201 (100) | SI | 0.256 (29) | 0.071 (100) | 0.046 (100) | — | — |
| | Total | 0.909 | 2.23 | 1.736 | 1.315 | 0.896 | 0.922 | 0.534 | 0.394 | 0.214 | — |
| 38 | Top | 2.172 (92) | 5.664 (92) | 5.323 (95) | 4.257 (96) | 3.374 (92) | 2.505 (89) | 1.795 (87) | 1.447 (80) | 0.890 (86) | — |
| | Bottom | 0.450 (92) | 0.532 (94) | 0.305 (97) | 0.151 (100) | SI | 0.078 (56) | 0.026 (100) | 0.019 (100) | — | — |
| | Total | 2.622 | 6.196 | 5.628 | 4.408 | 3.374 | 2.583 | 1.821 | 1.466 | 0.890 | — |
| 39 | Top | 0.021 (95) | 0.360 (93) | 0.589 (96) | 0.534 (98) | 0.404 (93) | 0.260 (91) | 0.172 (86) | 0.129 (81) | 0.071 (85) | — |
| | Bottom | 0.076 (95) | 0.223 (90) | 0.174 (97) | 0.095 (100) | SI | 0.021 (100) | 0.013 (100) | 0.008 (100) | 0.041 (100) | — |
| | Total | 0.097 | 0.583 | 0.763 | 0.629 | 0.404 | 0.281 | 0.185 | 0.137 | 0.079 | — |
| 40 | Top | 0.394 (95) | 1.871 (96) | 1.789 (97) | 1.334 (95) | 0.912 (94) | 0.564 (92) | 0.335 (87) | 0.224 (82) | 0.121 (86) | — |
| | Bottom | 0.466 (95) | 0.674 (96) | 0.300 (100) | 0.111 (100) | SI | 0.017 (100) | — | — | — | — |
| | Total | 0.860 | 2.54 | 2.089 | 1.445 | 0.912 | 0.581 | 0.335 | 0.224 | 0.121 | — |
| 41 | Single | — | 0.035 (100) | — | — | SI | 0.062 (100) | 0.031 (100) | 0.027 (100) | 0.022 (100) | — |
| 42 | Single | — | 0.023 | — | 0.005 (100) | SI | 0.111 (81) | 0.028 (100) | — | — | — |
| 43 | Single | 0.019 (100) | 0.077 (58) | 0.047 (100) | 0.046 (100) | SI | 0.096 (42) | 0.032 (100) | 0.005 (100) | 0.005 (100) | — |
| 44 | Single | 4.166 (80) | 0.304 (30) | 0.014 (80) | 0.002 (81) | 0.004 (100) | 0.006 (100) | 0.007 (100) | 0.103 (100) | 0.041 (100) | — |
| 45 | Single | 7.312 (96) | 11.817 (94) | 6.173 (96) | 2.680 (94) | 1.262 (93) | 0.519 (100) | 0.239 (100) | 0.062 (100) | 0.008 (100) | — |
| 46 | Single | 10.348 (62) | 8.095 (60) | 2.861 (66) | 0.877 (77) | 0.431 (63) | 0.165 (68) | 0.067 (71) | 0.003 (100) | 0.029 (66) | — |
| 47 | Single | 0.07 (93) | 0.107 (95) | 0.066 (100) | 0.038 (100) | 0.020 (100) | 0.013 (77) | 0.005 (100) | 0.045 (53) | — | — |
| 48 | Single | 3.381 (89) | 0.213 (43) | 0.034 (93) | 0.047 (100) | 0.051 (89) | 0.036 (93) | 0.045 (44) | 0.043 (44) | 0.045 (45) | — |
| 49 | Top | 0.156 (94) | 3.517 (98) | 3.508 (96) | 3.134 (98) | 3.309 (93) | 2.367 (89) | 2.004 (85) | 1.880 (89) | 1.506 | — |
| | Bottom | 0.066 (92) | 0.662 (88) | 0.318 (95) | 0.143 (100) | SI | 0.164 (24) | 0.025 (100) | 0.027 (73) | 0.086 (26) | — |
| | Total | 0.222 | 4.179 | 3.826 | 3.277 | 3.309 | 2.531 | 2.029 | 1.907 | 1.592 | — |
| 50 | Top | 2.052 (91) | 3.706 (90) | 3.372 (94) | 2.896 (98) | 2.739 (90) | 2.225 (91) | 1.712 (94) | 1.370 (96) | 0.866 (100) | — |
| | Bottom | 0.366 (73) | 0.339 (89) | 0.147 (93) | 0.059 (100) | SI | 0.027 (57) | 0.011 (100) | 0.023 (39) | 0.046 (16) | — |
| | Total | 2.418 | 4.045 | 3.519 | 2.955 | 2.739 | 2.252 | 1.723 | 1.393 | 0.912 | — |
| 51 | Top | 0.493 (38) | 2.477 (42) | 2.828 (54) | 1.884 (84) | 2.177 (61) | 1.704 (66) | 1.330 (68) | 1.126 (72) | 0.814 (78) | — |
| | Bottom | 0.063 (36) | 0.510 (44) | 0.232 (57) | 0.076 (100) | — | 0.043 (69) | 0.024 (100) | 0.017 (100) | 0.015 (100) | — |
| | Total | 0.556 | 2.987 | 3.060 | 1.960 | 2.127 | 1.747 | 1.354 | 1.143 | 0.829 | — |
| 52 | Top | 0.223 (88) | 1.048 (92) | 1.419 (94) | 1.436 (98) | 2.750 (48) | 1.297 (90) | 1.174 (86) | 1.115 (85) | 0.921 (85) | — |
| | Bottom | 0.066 (49) | 0.115 (93) | 0.103 (100) | 0.058 (100) | SI | 0.015 (100) | 0.009 (100) | 0.006 (100) | 0.005 (100) | — |
| | Total | 0.289 | 1.163 | 1.522 | 1.494 | 2.750 | 1.312 | 1.183 | 1.121 | 0.926 | — |
| 53 | Single | 0.773 (96) | 1.350 (91) | 1.081 (98) | 0.822 (95) | 0.602 (95) | 0.400 (94) | 0.269 (90) | 0.203 (82) | 0.119 (86) | — |
| 54 | Top | 2.233 (93) | 4.506 (92) | 4.841 (95) | 4.305 (96) | 3.860 (92) | 3.150 (90) | 2.371 (88) | 1.873 (84) | 1.113 (90) | — |
| | Bottom | 0.334 (92) | 0.314 (95) | 0.180 (100) | 0.087 (100) | SI | 0.047 (56) | 0.017 (100) | 0.014 (100) | — | — |
| | Total | 2.567 | 4.82 | 5.021 | 4.392 | 3.860 | 3.197 | 2.388 | 1.887 | 1.113 | — |
| 55 | Single | 0.113 (100) | 0.288 (100) | 0.460 (100) | 0.372 (100) | 0.338 (100) | 0.281 (100) | 0.248 (100) | 0.242 (100) | 0.260 (100) | — |
| 56 | Top | 3.481 (97) | 6.328 (96) | 6.159 (97) | 5.048 (95) | 4.134 (95) | 3.215 (94) | 2.445 (90) | 1.941 (90) | 1.337 (91) | 1.140 (98) |
| | Bottom | 0.424 (90) | 0.292 (100) | 0.163 (100) | 0.083 (100) | 0.047 (100) | 0.030 (100) | 0.022 (100) | 0.015 (100) | — | — |
| | Total | 3.905 | 6.62 | 6.322 | 5.131 | 4.181 | 3.245 | 2.467 | 1.956 | 1.337 | 1.140 |

TABLE III-continued

| Example | Phase | OLEFIN (WT. %) (ALPHA-OLEFIN WT. % OF OLEFIN) | | | | | | | | | |
|---|---|---|---|---|---|---|---|---|---|---|---|
| | | $C_4$ | $C_6$ | $C_8$ | $C_{10}$ | $C_{12}$ | $C_{14}$ | $C_{16}$ | $C_{18}$ | $C_{20}$ | $C_{22}$ |
| 57 | Top | 1.969 (86) | 4.433 (86) | 4.826 (90) | 4.102 (94) | 3.755 (87) | 3.105 (86) | 2.565 (82) | 2.354 (77) | 1.597 (82) | 1.316 (94) |
| | Bottom | 0.387 (86) | 0.276 (80) | 0.132 (89) | 0.058 (100) | SI | 0.014 (100) | 0.012 (100) | 0.011 (100) | — | — |
| | Total | 2.356 | 4.700 | 4.958 | 4.16 | 3.755 | 3.119 | 2.577 | 2.365 | 1.597 | 1.316 |
| 58 | Top | 1.704 (90) | 4.301 (87) | 4.754 (92) | 4.135 (96) | 3.741 (87) | 3.072 (86) | 2.552 (83) | 2.356 (78) | 1.562 (81) | 1.260 (90) |
| | Bottom | 0.265 (84) | 0.241 (90) | 0.146 (93) | 0.079 (100) | SI | 0.028 (100) | 0.019 (100) | 0.011 (100) | — | — |
| | Total | 1.969 | 4.542 | 4.900 | 4.214 | 3.741 | 3.100 | 2.571 | 2.367 | 1.562 | 1.260 |
| 59 | Distilled | 30.562 (99) | 1.40 (81) | — | — | — | — | — | — | — | — |
| | Residual | 0.326 (97) | 3.414 (76) | 0.771 (94) | 0.185 (78) | 0.116 (88) | 0.105 (89) | 0.090 (86) | 0.74 (88) | 0.39 (97) | 0.45 (100) |
| | Top | | | | | | | | | | |
| | Bottom | 1.100 (92) | 0.871 (71) | 0.063 (100) | 0.038 (100) | — | — | — | — | — | — |
| | Total | 31.99 | 5.685 | 0.834 | 0.223 | 0.116 | 0.105 | 0.090 | 0.74 | 0.39 | 0.45 |
| 60 | Single | 0.098 (76) | 0.089 (83) | 0.158 (85) | 0.165 (100) | SI | 0.192 (81) | 0.155 (91) | 0.118 (100) | 0.077 (100) | 0.676 (100) |
| 61 | Top | 3.637 (98) | 4.5190 (97) | 3.715 (99) | 2.915 (94) | SI | 1.690 (97) | 1.348 (97) | 1.064 (99) | 0.844 (100) | — |
| | Bottom | 0.599 (98) | 0.473 (99) | 0.265 (99) | 0.157 (86) | SI | 0.029 (100) | 0.016 (100) | 0.009 (100) | 0.006 (100) | — |
| | Total | 4.236 | 4.992 | 3.98 | 3.072 | SI | 1.719 | 1.364 | 1.073 | 0.850 | 0.676 |
| 62 | Single | 0.607 (92) | 0.166 (87) | 0.338 (96) | 0.357 (76) | SI | 0.093 (100) | 0.052 (100) | 0.031 (100) | 0.019 (100) | 0.574 (94) |
| 63 | Top | 6.457 (96) | 9.285 (94) | 7.511 (96) | 5.528 (92) | SI | 2.750 (87) | 1.958 (84) | 1.443 (78) | 0.941 (85) | — |
| | Bottom | 1.110 (95) | 0.736 (92) | 0.346 (95) | 0.184 (73) | SI | 0.031 (100) | 0.019 (100) | 0.010 (100) | — | — |
| | Total | 7.567 | 10.021 | 7.857 | 5.712 | SI | 2.781 | 1.977 | 1.453 | 0.941 | 0.574 |
| 64 | Distilled | 22.660 (98) | 1.876 (78) | 0.078 (100) | 0.004 (100) | — | — | — | — | — | — |
| | Top | | | | | | | | | | |
| | Residual | 0.719 (97) | 4.956 (77) | 1.486 (92) | 0.303 (65) | 0.069 (67) | 0.027 (76) | 0.018 (80) | 0.013 (80) | 0.009 (96) | 0.006 (100) |
| 65 | Top | 1.622 (38) | 1.079 (66) | 0.186 (47) | 0.056 (32) | — | 0.027 | 0.002 (100) | 0.013 | 0.031 (100) | 0.006 |
| | Bottom | 25.001 | 7.911 | 1.75 | 0.363 | .609 | — | 0.020 | — | 0.040 | — |
| | Total | | | | | | | | | | |
| 66 | Top | 2.381 (97) | 0.327 (90) | 0.22 (100) | 0.233 (52) | SI | 0.019 (100) | 0.014 (100) | 0.08 (100) | — | — |
| 67 | Bottom | 3.113 (70) | 4.078 (.86) | 0.830 (95) | 0.233 (100) | SI | 0.019 | 0.014 | 0.08 | — | — |
| | Single | 5.494 | 4.405 | 0.852 | 0.031 (100) | SI | 0.011 (100) | | | | |
| | Distilled | 0.012 (100) | 0.014 (100) | 0.009 (100) | | | | | | | |
| | Top | 8.716 (50) | 7.289 (96) | 0.650 (100) | | | | | | | |
| | Residual | | | | | | | | | | |
| | Top | 5.402 (97) | 8.735 (93) | 7.151 (97) | 4.958 (96) | 3.342 (93) | 2.188 (92) | 1.476 (88) | 1.034 (82) | 0.643 (88) | 0.369 (98) |
| | Bottom | 0.003 (100) | 0.769 (93) | 0.381 (96) | 0.200 (78) | — | 0.043 (100) | 0.025 (100) | 0.013 (100) | 0.007 (100) | — |
| | Total | 14.121 | 16.793 | 8.182 | 5.158 | 3.342 | 2.233 | 1.501 | 1.047 | 0.650 | 0.369 |
| 68 | Top | 5.590 (98) | 7.874 (95) | 6.528 (97) | 4.728 (96) | 3.245 (96) | 2.167 (94) | 1.434 (90) | 0.961 (83) | 0.584 (87) | 0.330 (97) |
| | Bottom | 0.915 (98) | 0.601 (92) | 0.252 (97) | 0.123 (77) | SI | 0.022 (100) | 0.011 (100) | 0.006 (100) | 0.004 (100) | — |
| | Total | 6.505 | 8.475 | 6.78 | 4.851 | 3.245 | 2.189 | 1.445 | 0.967 | 0.588 | 0.330 |
| 69 | Top | 2.835 (88) | 4.564 (90) | 3.953 (94) | 2.580 (99) | 1.686 (95) | 1.020 (94) | 0.617 (88) | 0.381 (85) | 0.210 (89) | 0.110 (98) |
| | Bottom | 1.200 (86) | 0.664 (87) | 0.332 (92) | 0.183 (78) | SI | 0.037 (92) | 0.016 (100) | 0.007 (100) | 0.003 (100) | — |
| | Total | 4.035 | 5.228 | 4.285 | 2.763 | 1.686 | 1.057 | 0.633 | 0.388 | 0.213 | 0.110 |
| 70 | Top | 3.661 (91) | 5.893 (88) | 5.305 (93) | 4.042 (90) | 3.023 (88) | 2.124 (86) | 1.597 (79) | 1.341 (74) | 0.857 (81) | 0.529 (92) |
| | Bottom | 0.805 (90) | 0.444 (71) | 0.217 (92) | 0.094 (71) | SI | 0.023 (100) | 0.013 (100) | 0.006 (100) | 0.004 (100) | — |
| | Total | 4.466 | 6.337 | 5.522 | 4.136 | 3.023 | 2.147 | 1.58 | 1.347 | 0.861 | 0.529 |
| 71 | Top | 1.495 (98) | 5.683 (96) | 5.188 (98) | 3.645 (96) | 2.397 (96) | 1.561 (94) | 1.00 (90) | 0.683 (87) | 0.378 (90) | 0.259 (98) |
| | Bottom | 0.853 (97) | 0.894 (83) | 0.449 (98) | 0.267 (83) | SI | 0.067 (100) | 0.040 (100) | 0.025 (100) | 0.013 (100) | — |
| | Total | 2.348 | 6.577 | 5.637 | 3.912 | 2.397 | 1.628 | 1.040 | 0.708 | 0.391 | 0.259 |
| 72 | Distilled | 0.354 (98) | 0.056 (97) | — | — | — | — | — | — | — | — |
| | Top | | | | | | | | | | |
| | Residual | 2.333 (49) | 4.318 (96) | 4.651 (97) | 3.616 (96) | 2.497 (95) | 1.671 (94) | 1.114 (90) | 0.793 (87) | 0.459 (90) | — |
| | Bottom | 1.452 (97) | 0.898 (63) | 0.368 (98) | 0.162 (78) | SI | 0.021 (100) | 0.011 (100) | 0.006 (100) | — | — |
| | Total | 4.139 | 5.272 | 5.019 | 3.778 | 2.497 | 1.692 | 1.125 | 0.799 | 0.459 | — |

TABLE IV

| Example | GC Total C$_4$ to C$_{20}$ (wt. %) | Catalyst Dump Weight (grams) | GC Total C$_4$ to C$_{20}$ (grams) | Product Make by Mass Balance (grams) | Run Time (hours) | Average Reaction Rate to C$_4$ to C$_{20}$ - Calculated (gram-mol/L/hr) |
|---|---|---|---|---|---|---|
| 1 | — | — | — | — | — | — |
| 2 | — | — | — | — | — | — |
| 3 | — | — | — | — | — | — |
| 4 | — | — | — | — | — | — |
| 5 | — | — | — | — | — | — |
| 6 | — | — | — | — | — | — |
| 7 | — | — | — | — | — | — |
| 8 | — | — | — | — | — | — |
| 9 | — | — | — | — | — | — |
| 10 | — | — | — | — | — | — |
| 11 | — | — | — | — | — | — |
| 12 | — | — | — | — | — | — |
| 13 | — | — | — | — | — | — |
| 14 | — | — | — | — | — | — |
| 15 | — | — | — | — | — | — |
| 16 | 25.53 | 71.9 | 18.36 | — | 1.6 | 11.7 |
| 17 | 6.28 | 49.08 | 3.08 | — | 1.1 | 2.86 |
| 18 | 8.43 | 49.71 | 4.19 | — | 1.4 | 3.05 |
| 19 | 5.91 | 53.5 | 3.16 | 10.39 | 1.2 | 2.84 |
| 20 | 25.53 | 71.9 | 18.36 | 24.9032 | 1.6 | 11.7 |
| 21 | 38.46 | 85.1 | 32.73 | 39.79 | 0.5 | 66.7 |
| 22 | 26.17 | 70.5 | 18.45 | 25.69 | 0.5 | 37.6 |
| 23 | 40.06 | 84.8 | 33.97 | 38.87 | 0.5 | 69.2 |
| 24 | 40.42 | 84.8 | 34.70 | 38.98 | 0.5 | 70.68 |
| 25 | 17.59 | 63.9 | 11.24 | 18.02 | 0.9 | 12.72 |
| 26 | 6.01 | 37.21 | 2.236 | 7.126 | 1.0 | 2.28 |
| 27 | 11.55 | 38.00 | 4.39 | 7.900 | 1.0 | 4.47 |
| 28 | 7.52 | 55.00 | 4.136 | 8.868 | 1.0 | 4.21 |
| 29 | 6.62 | 55.80 | 3.69 | 13.52 | 1.0 | 3.76 |
| 30 | 0.825 | 52.00 | 0.43 | 1.30 | 0.9 | 0.49 |
| 31 | 8.11 | 45.58 | 3.70 | 8.14 | 1.1 | 3.77 |
| 32 | 7.26 | 52.00 | 3.78 | 7.71 | 1.3 | 2.96 |
| 33 | 15.29 | 43.41 | 6.64 | 13.34 | 0.75 | 18.12 |
| 34 | 41.27 | 57.0 | 23.52 | 27.01 | 0.5 | 55.02 |
| 35 | 46.09 | 71.5 | 32.95 | 41.7 | 0.5 | 67.11 |
| 36 | 30.56 | 56.0 | 17.11 | — | 0.5 | 34.85 |
| 37 | 8.73 | 50.79 | 4.433 | 6.712 | 1.5 | 3.01 |
| 38 | 28.988 | 74.6 | 21.6 | 28.2 | 1.5 | 14.7 |
| 39 | 3.16 | 54.012 | 1.71 | 5.26 | 2.4 | 0.73 |
| 40 | 9.11 | 60.10 | 5.47 | 10.34 | 1.2 | 4.65 |
| 41 | 0.128 | 52.1 | 0.067 | 6.38 | 1.1 | 0.06 |
| 42 | 0.216 | 45.87 | 0.099 | 0.1275 | 1.0 | 0.10 |
| 43 | 0.271 | 46.4 | 0.126 | 0.5151 | 1.2 | 0.11 |
| 44 | 4.513 | 34.02 | 1.536 | 2.585 | 1.3 | 1.20 |
| 45 | 30.146 | 53.2859 | 16.064 | 21.91 | 1.0 | 16.36 |
| 46 | 22.945 | 46.9611 | 10.775 | 15.608 | 1.5 | 7.32 |
| 47 | 0.322 | 30.8468 | 0.0993 | −0.342 | 0.5 | 0.20 |
| 48 | 3.895 | 32.092 | 1.25 | 2.26 | 0.5 | 2.55 |
| 49 | 22.572 | 76.44 | 17.254 | 30.536 | 0.5 | 35.14 |
| 50 | 22.12 | 21.39 | 15.791 | 26.74 | 0.3 | 53.61 |
| 51 | 15.76 | 73.0 | 11.51 | 26.8113 | 0.4 | 29.31 |
| 52 | 11.76 | 52.80 | 6.21 | 7.348 | 1.2 | 5.27 |
| 53 | 5.619 | 38.03 | 2.14 | 8.0545 | 0.7 | 3.11 |
| 54 | 28.327 | 85.20 | 24.13 | 38.931 | 1.0 | 24.58 |
| 55 | 2.602 | 47.0 | 1.223 | 3.10 | 1.0 | 1.25 |
| 56 | 35.164 | 79.0 | 27.78 | 33.52 | 0.4 | 70.7 |
| 57 | 29.587 | 73.4 | 21.72 | 28.81 | 0.5 | 44.2 |
| 58 | 28.966 | 75.2 | 21.78 | 30.22 | 0.5 | 44.2 |
| 59 | 39.156 | 68.2 | 26.70 | 22.70 | 1.1 | 24.7 |
| 60 | 1.052 | 49.0 | 0.52 | 3.80 | 2.5 | 0.21 |
| 61 | 21.294 | 66.0 | 14.05 | 20.59 | 0.5 | 28.62 |
| 62 | 1.663 | 47.8 | 0.795 | 2.1 | 0.75 | 1.08 |
| 63 | 35.309 | 77.0 | 27.19 | 32.0 | 0.33 | 83.9 |
| 64 | 35.194 | 81.0 | 28.51 | 35.39 | 0.4 | 72.6 |
| 65 | 11.025 | 58.7 | 6.47 | 12.9 | 1.0 | 6.69 |
| 66 | 0.77 | 52.7 | 0.041 | 7.22 | 1.0 | 0.042 |
| 67 | 53.027 | 7.77 | 41.20 | 31.4 | 1.3 | 32.28 |
| 68 | 34.748 | 75.8 | 26.34 | 30.3 | 1.0 | 26.8 |
| 69 | 28.288 | 64.3 | 13.05 | 18.8 | 1.0 | 13.3 |
| 70 | 29.419 | 67.2 | 19.77 | 22.2 | 0.6 | 33.56 |
| 71 | 26.413 | 55.2 | 14.58 | 10.6 | 1.0 | 14.85 |
| 72 | 24.78 | 71.8 | 17.81 | 26.8 | 1.0 | 18.14 |

I claim:

1. An oligomerization or cooligomerization process comprising passing ethylene or a mixture of ethylene and propylene in contact with a catalyst, in the liquid phase, said catalyst comprising the reaction product of (i) a transition metal compound wherein the transition metal is selected from the group consisting of nickel, chromium, cobalt, iron, and copper, and mixtures thereof; (ii) in the event that (a) the transition metal is not in the oxidation state of zero or (b) the transition metal compound does not have a hydride or an alkyl, alkenyl, alkynyl, or aryl group bonded to the transition metal, a catalyst activator consisting of a compound or compounds capable of transferring a hydride or an alkyl, alkenyl, alkynyl, or aryl group from itself to the transition metal/ligand, hereinafter defined, complex formed by the reaction of the transition metal compound with the ligand and bonding the group to the transition metal, said activator being present in a sufficient amount to activate the catalyst; and (iii) at least one organophosphorus sulfonate ligand containing (a) at least one benzene ring having a trivalent phosphorus atom located at one position on the benzene ring and an $SO_3M$ group located at a position on the benzene ring ortho thereto, or at least one benzene ring having a trivalent phosphorus atom connected through a methylene group to a first position on the benzene ring and an $SO_3M$ group connected through a methylene group to a second position on the benzene ring ortho to the first position, or at least one bridging or fused aromatic ring system having a trivalent phosphorus atom and and $SO_3M$ group, each located on a different aromatic ring in the system at substituent positions adjacent to one another, or at least one aromatic ring, other than a benzene ring, or heteroaromatic ring, each ring having a trivalent phosphorus atom and an $SO_3M$ group located at substituent positions adjacent to one another, wherein M is selected from the group consisting of hydrogen, alkali metals, alkaline earth metals, and $NR_4$ and $PR_4$ wherein R is a hydrogen atom or a substituted or unsubstituted hydrocarbyl radical having 1 to 15 carbon atoms and each R can be alike or different or (b) a trivalent phosphorus atom connected through a group having the formula

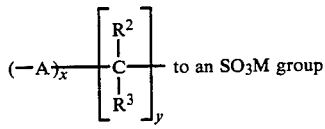

wherein A is an oxygen atom, an NH radical, or an NR radical; $R^2$ and $R^3$ are hydrogen atoms or a substituted or unsubstituted hydrocarbyl radical having 1 to 6 carbon atoms and can be alike or different; x is an integer 0 or 1; y is an integer from 1 to 3; and R and M are as defined above.

2. The process defined in claim 1 wherein the catalyst activator is selected from the group consisting of borohydrides, aryl boranes, $BH_3$, mono-, di-, and trialkyl boranes, aryl borates, tri and tetra coordinate organoaluminum compounds, aluminum hydrides, tri and tetra alkyl boron compounds, organozinc compounds, and mixtures thereof.

3. The process defined in claims 1 or 2 wherein the transition metal compound is a hydrated salt.

4. The process defined in claim 3 wherein the hydrated salt is selected from the group consisting of halides, sulfonates, tetrafluoroborates, and mixtures thereof.

5. The process defined in claim 3 wherein the transition metal is nickel.

6. The process defined in claim 2 wherein the catalyst activator is a borohydride selected from the group consisting of alkali metal borohydrides, quaternary ammonium borohydrides, alkali metal alkoxyborohydrides, phenoxyborohydrides, or amidoborohydrides, and mixtures thereof.

7. The process defined in claim 2 wherein the catalyst activator is selected from the group consisting of aryl boranes, $BH_3$, mono-, di-, and trialkyl boranes, aryl borates, and mixtures thereof.

8. The process defined in claims 1 or 2 wherein the organophosphorus sulfonate ligand is in the alkali metal salt form.

9. The process defined in claims 1 or 2 wherein the ligand is an ortho-phosphorus sulfonate represented by the following structural formula:

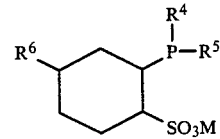

wherein $R^4$, $R^5$, $R^6$ are hydrogen atoms or substituted or unsubstituted hydrocarbyl radicals having 1 to 20 carbon atoms and can be alike or different; $R^4$ and $R^5$ can be connected to form a heterocyclic radical; and M is as set forth above.

10. The process defined in claims 1 or 2 wherein the ligand is an alkylene-phosphinosulfonate represented by the following structural formula:

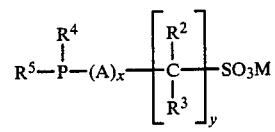

wherein $R^2$, $R^3$, A, M, x, and y are as set forth above, and $R^4$ and $R^5$ are hydrogen atoms or substituted or unsubstituted hydrocarbyl radicals having 1 to 20 carbon atoms, can be alike or different, and can be connected to form a heterocyclic radical.

11. The process defined in claim 9 wherein $R^4$, $R^5$, and $R^6$ are selected from the group consisting of hydrogen atoms or alkyl, aryl, alkoxy, aroxy, amino, or amido radicals, or mixtures thereof.

12. The process defined in claim 10 wherein $R^4$ and $R^5$ are selected from the group consisting of hydrogen atoms or alkyl, aryl, alkoxy, aroxy, amino, or amido radicals, or mixtures thereof.

13. The process defined in claims 1 or 2 wherein the process is carried out in water.

14. The process defined in claims 1 or 2 wherein the process is carried out in sulfolane.

15. The process defined in claim 2 wherein the catalyst activator is selected from the group consisting of tri- or tetra coordinate aluminum compounds, aluminum hydrides, tri- or tetra alkyl boron compounds, and organozinc compounds.

* * * * *

UNITED STATES PATENT AND TRADEMARK OFFICE
CERTIFICATE OF CORRECTION

PATENT NO. : 4,689,437
DATED : August 25, 1987
INVENTOR(S) : Rex Eugene Murray

It is certified that error appears in the above-identified patent and that said Letters Patent is hereby corrected as shown below:

Column 6, line 1 to 8, and column 34, lines 19 to 20, change " 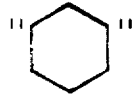 " to --  --

Column 32, third line from bottom, after "phase,", insert

--under oligomerization conditions,--.

Signed and Sealed this

Tenth Day of October, 1989

Attest:

DONALD J. QUIGG

Attesting Officer

Commissioner of Patents and Trademarks